(12) United States Patent
Rishel et al.

(10) Patent No.: US 8,008,500 B2
(45) Date of Patent: Aug. 30, 2011

(54) INTERMEDIATES USEFUL FOR MAKING TETRABENAZINE COMPOUNDS

(75) Inventors: Michael James Rishel, Rensselaer, NY (US); Kande Kankananamalage Dayarathna Amarasinghe, Latham, NY (US); Sean Richard Dinn, Delmar, NY (US); Bruce Fletcher Johnson, Scotia, NY (US)

(73) Assignee: General Electric Company, Niskayuna, NY (US)

( * ) Notice: Subject to any disclaimer, the term of this patent is extended or adjusted under 35 U.S.C. 154(b) by 903 days.

(21) Appl. No.: 11/760,372

(22) Filed: Jun. 8, 2007

(65) Prior Publication Data

US 2008/0306269 A1 Dec. 11, 2008

(51) Int. Cl.
*C07D 217/00* (2006.01)
(52) U.S. Cl. ......................................... 546/147; 546/150
(58) Field of Classification Search .................. None
See application file for complete search history.

(56) References Cited

U.S. PATENT DOCUMENTS

| | | | |
|---|---|---|---|
| 3,132,147 | A | 5/1964 | Schopf et al. |
| 4,193,998 | A | 3/1980 | Szantay et al. |
| 4,686,226 | A | 8/1987 | Huff et al. |
| 5,118,690 | A | 6/1992 | Minchin et al. |
| 5,272,270 | A | 12/1993 | Hirsenkorn et al. |
| 5,278,308 | A | 1/1994 | Kung |
| 2002/0055637 | A1 | 5/2002 | Liu et al. |
| 2004/0082647 | A1 | 4/2004 | Babiak et al. |

FOREIGN PATENT DOCUMENTS

| | | |
|---|---|---|
| WO | WO2007017654 A1 | 2/2007 |
| WO | WO2007130365 A2 | 11/2007 |

OTHER PUBLICATIONS

International Search Report, Sep. 9, 2008.*
Schachter et al., "Release of 5-Hydroxytryptamine by Benzoquinolizine Derivatives With Sedative Action", Science, vol. 126, pp. 507-508, Sep. 13, 1957.
Huntington Study Group, "Tetrabenazine as Antichorea Therapy in Huntington Diease", Neurology, vol. 66, No. 3, pp. 366-372, 2006.
Narasaka et al., "Oxidative Generation of N-Acyliminium Ions From N-1-(Tributylstannyl)alkyl Carboxamides and Carbamates and Their Reactions With Carbon Nucleophiles", Bull. Chem. Soc., Japan, vol. 66, No. 11, pp. 3456-3463, Nov. 1993.
Fürstner, "Carbon-Carbon Bond Formations Involving Organochromium(III) Reagents", Chem. Rev., vol. 99, No. 4, pp. 991-1045, 1999.
Koeppe et al., "Kinetic Evaluation of [11C]Dihydrotetrabenazine by Dynamic—PET: Measurement of Vesicular Monoamine Transporter", Journal of Cerebral Blood Flow and Metabolism, vol. 16, No. 6, pp. 1288-1299, 1996.
Koeppe et al., "Assessment of Extrastriatal Vesicular Monoamine Transporter Binding Site Density Using Stereoisomers of [11C]Dihydrotetrabenazine", Journal of Cerebral Blood Flow and Metabolism, vol. 19, No. 12, pp. 1376-1384, 1999.
Sasamoto et al., "Pd(II)-Catalyzed Asymmetric Addition of Malonates to Dihydroisoquinolines", J. Am. Chem. Soc., vol. 128, No. 43, pp. 14010-14011, 2006.
von A. Brossi et al., "Syntheseversuche in der Emetin-Reihe", Helvetica Chemica Acta, vol. 77, pp. 5830593, 1960.
Shimizu et al., "Novel Synthesis of Heterocycles Having a Functionalized Carbon Center via Nickel-Mediated Carboxylation: Total Synthesis of Erythrocarine", Organic Letters, vol. 5, No. 13, pp. 2323-2325, 2003.
Venkov et al., "Synthesis of 1-(2-Oxoalkyl)-2-Acyltetrahydro-Isoquinolines by alpha-Amidoalkylation of Methylene Active Carbonyl Compounds With N-Acyliminium Intermediates", Synthetic Communications, vol. 26, No. 11, pp. 2135-2144, 1996.
Co-Pending US Patent Application entitled, "Method for Making Tetrabenazine Compounds", Jun. 8, 2007.
European Search Report dated Nov. 10, 2010 and Written Opinion.
Venkov et al., "Synthesis of 1-(2-oxoalkyl)-2-acyltetrahydroisoquinolines by .alpha.-amidoalkylation of methylene active carbonyl compounds with N-acyliminium intermediates", XP002608784, retrieved from STN Database accession No. 1996:260456, RN: 177497-02-08, 177497-03-9 & Synthetic Communications, vol. 26, No. 11, 2135-44 Coden: SYNCAV; ISSN 0039-7911, 2 pages, 1996.
Naraska et al., "Oxidative generation of N-acyliminium ions from N-1-(tributylstannyl)alkyl carboxamides and carbamates and their reactions with carbon nucleophiles", XP002608785, retrieved from STN, Database accession No. 1994:191500, RN: 153749-77-0 & Bulletin of the Chemical Society of Japan, vol. 66, No. 11, 3456-63 Coden: BCXJA8, ISSN: 009-2673, 1 page, 1993.
Brossi et al., Synthesis in the emetine series, VII. Degradation and [new] synthesis of substituted 2-oxohydrobenzo [a]quinolizines:, XP002608786, retrieved from STN Database accession No. 1960:128994, RN: 102466-05-7; 108897-96-7; 110531-37-8 & Helvetica Chimica Acta, vol. 43, 583-93, Coden: HCACAV, ISSN: 0018-019, 4 pages, 1960.

(Continued)

*Primary Examiner* — Zinna Northington Davis
(74) *Attorney, Agent, or Firm* — Andrew J. Caruso

(57) ABSTRACT

A method of preparing a tetrabenazine compound (TBZ compound) having structure I comprising the steps of reacting a nucleophilic alkenyl species with aldehyde compound II and oxidizing the resultant allylic alcohol to provide enone III. The protecting group $P^1$ on the tetrahydroisoquinoline nitrogen is removed and the resultant deprotected intermediate is induced to undergo an amino cyclization reaction to provide a product TBZ compound having structure I. The method may be used to prepare either enantiomeric form of tetrabenazine; (+)-tetrabenazine or (−)-tetrabenazine. Alternatively the method may be adapted to provide a mixture enriched in one tetrabenazine enantiomer, a racemic mixture, or a diastereomeric mixture of tetrabenazine compounds. In addition, the present invention provides novel synthetic intermediate compositions which may be used to prepare either or both enantiomers of tetrabenazine, derivatives of tetrabenazine, and analogs of tetrabenazine.

23 Claims, No Drawings

OTHER PUBLICATIONS

Hanna et al., "A Synthetic Approach to the Tricyclic System of Forskolin from D-Galactose", Tetrahedron Letters, XP002608787 vol. 35, No. 36, pp. 6685-6688, 1994.

Maldaner et al., "A Stereoselective Entry to Tetrasubstituted Quinolizidines and the Puzzling Structural Assignment of the Lupin Alkaloid Plumerinine", XP002608788, Synlett, No. 8, pp. 1343-1346, Jul. 1, 2004.

Bach et al., "Synthesis of 6-Substituted 4-Hydroxy-2-Pyrones From Aldehydes by Addition of an Acetoacetate Equivalent, Dess-Martin Oxidation and Subsequent Cyclization", XP002608789, Synlett, No. 12, pp. 1974-1976, 2001.

Takai et al., "Selective Grignard-Type Carbonyl Addition of Alkenyl Halides Mediated by Chromium (II) Chloride", XP002608801, Tetrahedron Letters, vol. 24, No. 47, pp. 5281-5284, 1983.

Caroon et al., Synthesis and Antihypertensive Activity of a Series of Spiro [1,3,4,6,7,11b-hexahydro-2H-benzo[a] quinolizine-2.5'-oxazolidin-2'-one]s1, XP002608838, Journal of Medicinal Chemistry, vol. 26, No. 10, pp. 1426-1433, 1983.

\* cited by examiner

INTERMEDIATES USEFUL FOR MAKING TETRABENAZINE COMPOUNDS

BACKGROUND

This invention relates to tetrabenazine compounds (TBZ compounds) and methods for the preparation of said tetrabenazine compounds.

Since first reported on in 1957 (Pletscher, A. (1957) Release of 5-hydroxytryptamine by benzoquinolizine derivatives with sedative action, *Science* 126, 507), tetrabenazine and structurally related compounds have been widely investigated, and a number of TBZ compounds and derivatives of tetrabenazine have shown promise in the treatment of a variety of conditions affecting human health. For example, dihydrotetrabenazine has been identified as an agent for the treatment of schizophrenia and other psychoses (See for example WO 2007017654 A1), and tetrabenazine has shown promise as an agent in the treatment of Huntington's disease (*Neurology* (2006), 66(3), 366-372). Although most preparations used in biological studies of tetrabenazine and its derivatives have been carried out on racemates, in at least one instance the biological activity exhibited by enantiomers tested separately was highly differentiated (See Koeppe, R. A. et al. (1999) Assessment of extrastriatal vesicular monoamine transporter binding site density using stereoisomers of [11C]dihydrotetrabenazine, *J Cereb Blood Flow Metab* 19, 1376-1384).

Notwithstanding, the availability of tetrabenazine and derivatives of tetrabenazine in racemic and enantiomerically enriched forms, there is a need for improved synthetic methods which provide either or both enantiomers of tetrabenazine, derivatives of tetrabenazine, and analogs of tetrabenazine. In addition, there is a need to provide novel synthetic intermediate compositions which may be used to prepare either or both enantiomers of tetrabenazine, derivatives of tetrabenazine, and analogs of tetrabenazine.

The present invention provides both a new and efficient synthetic methodology which may be used to prepare either or both enantiomers of tetrabenazine, derivatives of tetrabenazine and analogs of tetrabenazine. In addition the present invention provides novel synthetic intermediate compositions which may be used to prepare either or both enantiomers of tetrabenazine, derivatives of tetrabenazine and analogs of tetrabenazine.

BRIEF DESCRIPTION

In one embodiment, the present invention provides a tetrahydroisoquinoline compound having structure III,

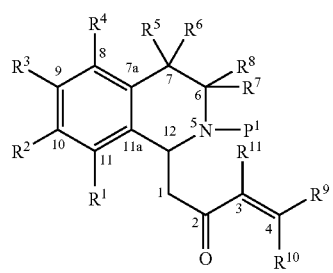

III wherein $R^1$-$R^4$ are independently hydrogen or an isotope thereof, a halogen atom, a $C_1$-$C_{20}$ aliphatic radical, a $C_2$-$C_{20}$ cycloaliphatic radical, or a $C_2$-$C_{20}$ aromatic radical, wherein at least one of $R^1$-$R^4$ is not hydrogen; $R^5$-$R^{11}$ are independently hydrogen or an isotope thereof, a $C_1$-$C_{20}$ aliphatic radical, a $C_2$-$C_{20}$ cycloaliphatic radical, or a $C_2$-$C_{20}$ aromatic radical; and $P^1$ is a protecting group.

In another embodiment, the present invention provides a tetrahydroisoquinoline compound having structure XI,

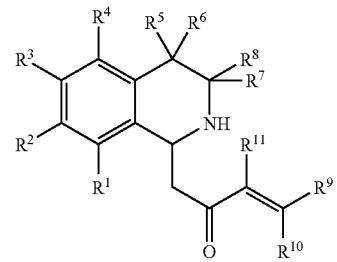

IX wherein $R^1$-$R^4$ are independently hydrogen or an isotope thereof, a halogen atom, a $C_1$-$C_{20}$ aliphatic radical, a $C_2$-$C_{20}$ cycloaliphatic radical, or a $C_2$-$C_{20}$ aromatic radical, wherein at least one of $R^1$-$R^4$ is not hydrogen; $R^5$-$R^{11}$ are independently hydrogen or an isotope thereof, a $C_1$-$C_{20}$ aliphatic radical, a $C_2$-$C_{20}$ cycloaliphatic radical, or a $C_2$-$C_{20}$ aromatic radical.

In yet another embodiment, the present invention provides a tetrahydroisoquinoline compound having structure XIII,

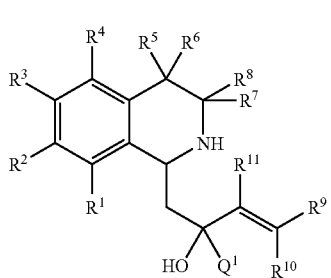

XIII wherein $R^1$-$R^4$ are independently hydrogen or an isotope thereof, a halogen atom, a $C_1$-$C_{20}$ aliphatic radical, a $C_2$-$C_{20}$ cycloaliphatic radical, or a $C_2$-$C_{20}$ aromatic radical, wherein at least one of $R^1$-$R^4$ is not hydrogen; $R^5$-$R^{11}$ are independently hydrogen or an isotope thereof, a $C_1$-$C_{20}$ aliphatic radical, a $C_2$-$C_{20}$ cycloaliphatic radical, or a $C_2$-$C_{20}$ aromatic radical; and $Q^1$ is hydrogen or an isotope thereof.

In yet another embodiment, the present invention provides tetrahydroisoquinoline compound having structure VII

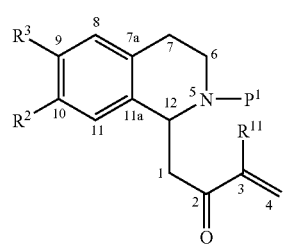

VII wherein $R^2$-$R^3$ are independently hydrogen or an isotope thereof, a halogen atom, a $C_1$-$C_{20}$ aliphatic radical, a $C_2$-$C_{20}$ cycloaliphatic radical, or a $C_2$-$C_{20}$ aromatic radical, wherein at least one of R²-R³ is not hydrogen; R¹¹ is hydrogen or an isotope thereof, a $C_1$-$C_{20}$ aliphatic radical, a $C_2$-$C_{20}$ cycloaliphatic radical, or a $C_2$-$C_{20}$ aromatic radical; and $P^1$ is a protecting group.

In yet another embodiment, the present invention provides a tetrahydroisoquinoline compound having structure XIV

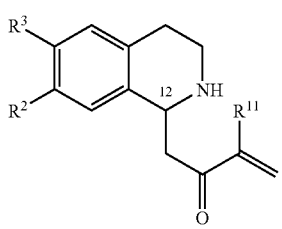

XIV wherein R²-R³ are independently hydrogen or an isotope thereof, a halogen atom, a $C_1$-$C_{20}$ aliphatic radical, a $C_2$-$C_{20}$ cycloaliphatic radical, or a $C_2$-$C_{20}$ aromatic radical, wherein at least one of R²-R³ is not hydrogen; and R¹¹ is hydrogen or an isotope thereof, a $C_1$-$C_{20}$ aliphatic radical, a $C_2$-$C_{20}$ cycloaliphatic radical, or a $C_2$-$C_{20}$ aromatic radical.

In yet another embodiment, the present invention provides a tetrahydroisoquinoline compound having structure XV.

XV

In yet another embodiment, the present invention provides a tetrahydroisoquinoline compound having structure XVI.

XVI

DETAILED DESCRIPTION

In the following specification and the claims, which follow, reference will be made to a number of terms, which shall be defined to have the following meanings.

The singular forms "a", "an" and "the" include plural referents unless the context clearly dictates otherwise.

"Optional" or "optionally" means that the subsequently described event or circumstance may or may not occur, and that the description includes instances where the event occurs and instances where it does not.

As used herein, the term "solvent" can refer to a single solvent or a mixture of solvents.

Approximating language, as used herein throughout the specification and claims, may be applied to modify any quantitative representation that could permissibly vary without resulting in a change in the basic function to which it is related. Accordingly, a value modified by a term or terms, such as "about", is not to be limited to the precise value specified. In some instances, the approximating language may correspond to the precision of an instrument for measuring the value.

As used herein, the term "aromatic radical" refers to an array of atoms having a valence of at least one comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. As noted, the aromatic radical contains at least one aromatic group. The aromatic group is invariably a cyclic structure having 4n+2 "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), anthraceneyl groups (n=3) and the like. The aromatic radical may also include nonaromatic components. For example, a benzyl group is an aromatic radical which comprises a phenyl ring (the aromatic group) and a methylene group (the nonaromatic component). Similarly a tetrahydronaphthyl radical is an aromatic radical comprising an aromatic group ($C_6H_3$) fused to a nonaromatic component —$(CH_2)_4$—. For convenience, the term "aromatic radical" is defined herein to encompass a wide range of functional groups such as alkyl groups, alkenyl groups, alkynyl groups, haloalkyl groups, haloaromatic groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylphenyl radical is a $C_7$ aromatic radical comprising a methyl group, the methyl group being a functional group which is an alkyl group. Similarly, the 2-nitrophenyl group is a $C_6$ aromatic radical comprising a nitro group, the nitro group being a functional group. Aromatic radicals include halogenated aromatic radicals such as 4-trifluoromethylphenyl, hexafluoroisopropylidenebis(4-phen-1-yloxy) (i.e., —OPhC(CF$_3$)$_2$PhO—), 4-chloromethylphen-1-yl, 3-trifluorovinyl-2-thienyl, 3-trichloromethylphen-1-yl (i.e., 3-CCl$_3$Ph-), 4-(3-bromoprop-1-yl)phen-1-yl (i.e., 4-BrCH$_2$CH$_2$CH$_2$Ph-), and the like. Further examples of aromatic radicals include 4-allyloxyphen-1-oxy, 4-aminophen-1-yl (i.e., 4-H$_2$NPh-), 3-aminocarbonylphen-1-yl (i.e., NH$_2$COPh-), 4-benzoylphen-1-yl, dicyanomethylidenebis(4-phen-1-yloxy) (i.e., —OPhC(CN)$_2$PhO—), 3-methylphen-1-yl, methylenebis(4-phen-1-yloxy) (i.e., —OPhCH$_2$PhO—), 2-ethylphen-1-yl, phenylethenyl, 3-formyl-2-thienyl, 2-hexyl-5-furanyl, hexamethylene-1,6-bis(4-phen-1-yloxy) (i.e., —OPh(CH$_2$)$_6$PhO—), 4-hydroxymethylphen-1-yl (i.e., 4-HOCH$_2$Ph-), 4-mercaptomethylphen-1-yl (i.e., 4-HSCH$_2$Ph-), 4-methylthiophen-1-yl (i.e., 4-CH$_3$SPh-), 3-methoxyphen-1-yl, 2-methoxycarbonylphen-1-yloxy (e.g., methyl salicyl), 2-nitromethylphen-1-yl (i.e., 2-NO$_2$CH$_2$Ph), 3-trimethylsilylphen-1-yl, 4-t-butyldimethylsilylphenl-1-yl, 4-vinylphen-1-yl, vinylidenebis(phenyl), and the like. The term "a $C_3$-$C_{10}$ aromatic radical" includes aromatic radicals containing at least three but no more than 10 carbon atoms. The aromatic radical 1-imidazolyl ($C_3H_2N_2$—) represents a $C_3$ aromatic radical. The benzyl radical ($C_7H_7$—) represents a $C_7$ aromatic radical.

As used herein the term "cycloaliphatic radical" refers to a radical having a valence of at least one, and comprising an array of atoms which is cyclic but which is not aromatic. As defined herein a "cycloaliphatic radical" does not contain an aromatic group. A "cycloaliphatic radical" may comprise one or more noncyclic components. For example, a cyclohexylmethyl group ($C_6H_{11}CH_2$—) is a cycloaliphatic radical which comprises a cyclohexyl ring (the array of atoms which is cyclic but which is not aromatic) and a methylene group (the noncyclic component). The cycloaliphatic radical may include heteroatoms such as nitrogen, sulfur, selenium, silicon and oxygen, or may be composed exclusively of carbon and hydrogen. For convenience, the term "cycloaliphatic radical" is defined herein to encompass a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylcyclopent-1-yl radical is a $C_6$ cycloaliphatic radical comprising a methyl group, the methyl group being a functional group which is an alkyl group. Similarly, the 2-nitrocyclobut-1-yl radical is a $C_4$ cycloaliphatic radical comprising a nitro group, the nitro group being a functional group. A cycloaliphatic radical may comprise one or more halogen atoms which may be the same or different. Halogen atoms include, for example; fluorine, chlorine, bromine, and iodine. Cycloaliphatic radicals comprising one or more halogen atoms include 2-trifluoromethylcyclohex-1-yl, 4-bromodifluoromethylcyclooct-1-yl, 2-chlorodifluoromethylcyclohex-1-yl, hexafluoroisopropylidene-2,2-bis(cyclohex-4-yl) (i.e., —$C_6H_{10}$C($CF_3$)$_2C_6H_{10}$—), 2-chloromethylcyclohex-1-yl, 3-difluoromethylenecyclohex-1-yl, 4-trichloromethylcyclohex-1-yloxy, 4-bromodichloromethylcyclohex-1-ylthio, 2-bromoethylcyclopent-1-yl, 2-bromopropylcyclohex-1-yloxy (e.g., $CH_3CHBrCH_2C_6H_{10}O$—), and the like. Further examples of cycloaliphatic radicals include 4-allyloxycyclohex-1-yl, 4-aminocyclohex-1-yl (i.e., $H_2C_6H_{10}$—), 4-aminocarbonylcyclopent-1-yl (i.e., $NH_2COC_5H_8$—), 4-acetyloxycyclohex-1-yl, 2,2-dicyanoisopropylidenebis(cyclohex-4-yloxy) (i.e., —$OC_6H_{10}C(CN)_2C_6H_{10}O$—), 3-methylcyclohex-1-yl, methylenebis(cyclohex-4-yloxy) (i.e., —$OC_6H_{10}CH_2C_6H_{10}O$—), 1-ethylcyclobut-1-yl, cyclopropylethenyl, 3-formyl-2-terahydrofuranyl, 2-hexyl-5-tetrahydrofuranyl, hexamethylene-1,6-bis(cyclohex-4-yloxy) (i.e., —$OC_6H_{10}(CH_2)_6C_6H_{10}O$—), 4-hydroxymethylcyclohex-1-yl (i.e., 4-$HOCH_2C_6H_{10}$—), 4-mercaptomethylcyclohex-1-yl (i.e., 4-$HSCH_2C_6H_{10}$—), 4-methylthiocyclohex-1-yl (i.e., 4-$CH_3SC_6H_{10}$—), 4-methoxycyclohex-1-yl, 2-methoxycarbonylcyclohex-1-yloxy (2-$CH_3OCOC_6H_{10}O$—), 4-nitromethylcyclohex-1-yl (i.e., $NO_2CH_2C_6H_{10}$—), 3-trimethylsilylcyclohex-1-yl, 2-t-butyldimethylsilylcyclopent-1-yl, 4-trimethoxysilylethylcyclohex-1-yl (e.g., ($CH_3O)_3SiCH_2CH_2C_6H_{10}$—), 4-vinylcyclohexen-1-yl, vinylidenebis(cyclohexyl), and the like. The term "a $C_3$-$C_{10}$ cycloaliphatic radical" includes cycloaliphatic radicals containing at least three but no more than 10 carbon atoms. The cycloaliphatic radical 2-tetrahydrofuranyl ($C_4H_7O$—) represents a $C_4$ cycloaliphatic radical. The cyclohexylmethyl radical ($C_6H_{11}CH_2$—) represents a $C_7$ cycloaliphatic radical.

As used herein the term "aliphatic radical" refers to an organic radical having a valence of at least one consisting of a linear or branched array of atoms which is not cyclic. Aliphatic radicals are defined to comprise at least one carbon atom. The array of atoms comprising the aliphatic radical may include heteroatoms such as nitrogen, sulfur, silicon, selenium and oxygen or may be composed exclusively of carbon and hydrogen. For convenience, the term "aliphatic radical" is defined herein to encompass, as part of the "linear or branched array of atoms which is not cyclic" a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylpent-1-yl radical is a $C_6$ aliphatic radical comprising a methyl group, the methyl group being a functional group which is an alkyl group. Similarly, the 4-nitrobut-1-yl group is a $C_4$ aliphatic radical comprising a nitro group, the nitro group being a functional group. An aliphatic radical may be a haloalkyl group which comprises one or more halogen atoms which may be the same or different. Halogen atoms include, for example; fluorine, chlorine, bromine, and iodine. Aliphatic radicals comprising one or more halogen atoms include the alkyl halides trifluoromethyl, bromodifluoromethyl, chlorodifluoromethyl, hexafluoroisopropylidene, chloromethyl, difluorovinylidene, trichloromethyl, bromodichloromethyl, bromoethyl, 2-bromotrimethylene (e.g., —$CH_2CHBrCH_2$—), and the like. Further examples of aliphatic radicals include allyl, aminocarbonyl (i.e., —$CONH_2$), carbonyl, 2,2-dicyanoisopropylidene (i.e., —$CH_2C(CN)_2CH_2$—), methyl (i.e., —$CH_3$), methylene (i.e., —$CH_2$—), ethyl, ethylene, formyl (i.e., —CHO), hexyl, hexamethylene, hydroxymethyl (i.e., —$CH_2OH$), mercaptomethyl (i.e., —$CH_2SH$), methylthio (i.e., —$SCH_3$), methylthiomethyl (i.e., —$CH_2SCH_3$), methoxy, methoxycarbonyl (i.e., $CH_3OCO$—), nitromethyl (i.e., —$CH_2NO_2$), thiocarbonyl, trimethylsilyl (i.e., ($CH_3)_3Si$—), t-butyldimethylsilyl, 3-trimethoxysilylpropyl (i.e., ($CH_3O)_3SiCH_2CH_2CH_2$—), vinyl, vinylidene, and the like. By way of further example, a $C_1$-$C_{10}$ aliphatic radical contains at least one but no more than 10 carbon atoms. A methyl group (i.e., $CH_3$—) is an example of a $C_1$ aliphatic radical. A decyl group (i.e., $CH_3(CH_2)_9$—) is an example of a $C_{10}$ aliphatic radical.

As noted, in one embodiment the present invention provides a method of preparing a TBZ compound having structure I. TBZ compounds are defined herein to include tetrabenazine, derivatives of tetrabenazine, and analogs of tetrabenazine. The terms "tetrabenazine compound" and "TBZ compounds" are used interchangeably and have the same meaning. Tetrabenazine itself is a man-made, biologically active compound, and the term "tetrabenazine" is defined herein to be either a racemic mixture of enantiomers XVII and XVIII, or an enantiomerically enriched mixture of enantiomers XVII and XVIII, or a single enantiomer XVII or XVIII. It will be clear from context which form of tetrabenazine is meant. The tetrabenazine compound having structure XVII is at times herein referred to as (+)-tetrabenazine. The tetrabenazine compound having structure XVIII is at times herein referred to as (−)-tetrabenazine. For convenience and clarity, the numbering system shown in structures I, XVII, XVIII and elsewhere has been adopted and is used throughout this application to specify the ring positions (RP) of the TBZ compounds discussed herein as well as the synthetic intermediates used in the method of the present invention.

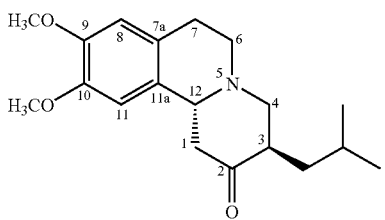

XVII

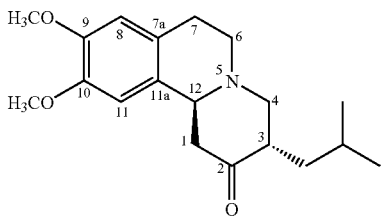

XVIII

The terms "derivatives of tetrabenazine", and "analogs of tetrabenazine" refer to TBZ compounds which are related to but are not identical to tetrabenazine. A derivative of tetrabenazine is a TBZ compound is derived from tetrabenazine (i.e., is made from tetrabenazine). An analog of tetrabenazine is a TBZ compound which is sufficiently related structurally to fall within the scope of generic structure I but is not identical to tetrabenazine itself. As with tetrabenazine itself, derivatives of tetrabenazine and analogs of tetrabenazine may be racemic, enantiomerically enriched mixtures of enantiomers, single enantiomers, or comprise a mixture of diastereomers. In one embodiment, the present invention provides a tetrabenazine compound having structure XVII in which ring positions 3 and 12 each possess the R configuration.

The tetrabenazine compounds produced by the method of the present invention may be "optically active", i.e. display an optical rotation measurable on a polarimeter. Alternatively, the tetrabenazene compounds produced by the method of the present invention may be "optically inactive", i.e. do not display an optical rotation measurable on a polarimeter. In various embodiments, the method of the present invention provides tetrabenazine compounds (TBZ compounds) having the same absolute stereochemistry shown in structure XVII, i.e. R configuration at ring positions 3 and 12. In various other embodiments, the method of the present invention provides tetrabenazine compounds having absolute stereochemistry opposite that shown in structure XVII, i.e. S configuration at ring positions 3 and 12.

In general, and throughout this disclosure, where no absolute or relative stereochemistry is shown for a structure, the structure is intended to encompass all possible absolute and relative stereochemical configurations. Thus, structure XIX depicts a tetrabenazine compound in which no absolute or relative stereochemistry is shown. As such, structure XIX is intended to represent a genus of tetrabenazine compounds which includes tetrabenazine having the R configuration at ring positions 3 and 12, a tetrabenazine compound having the opposite (S configuration) absolute stereochemistry at ring positions 3 and 12, racemic tetrabenazine containing a 1:1 mixture of enantiomer XVII and its 3-S/12-S enantiomer XVIII, and diastereomeric mixtures of tetrabenazine compounds, e.g. a mixture of tetrabenzine enantiomer XVII and a tetrabenazine compound having the same absolute (R configuration) stereochemistry at ring position-12 as enantiomer XVII, but possessing the S configuration at ring position-3. Representative tetrabenazine compounds encompassed by generic formula XIX are illustrated in Table 1. Those having ordinary skill in the art will appreciate that the individual compounds shown in Tables 1, 5, and 8 herein are illustrative of TBZ compounds falling within the scope of generic structure I.

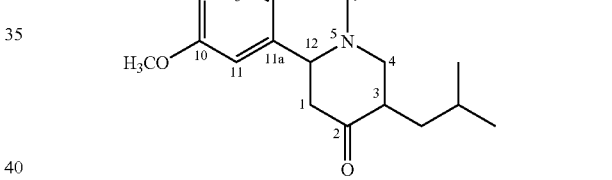

XIX

TABLE 1

Exemplary Tetrabenazine Compounds Encompassed By Generic Formula XIX

| Entry | Name | Ring Position* Stereochemistry | | Structure |
| | | RP-3 | RP-12 | |
| --- | --- | --- | --- | --- |
| 1a | Single "R,R" enantiomer of tetrabenazine | R | R | |

TABLE 1-continued

Exemplary Tetrabenazine Compounds Encompassed By Generic Formula XIX

| Entry | Name | Ring Position* Stereochemistry RP-3 | RP-12 | Structure |
|---|---|---|---|---|
| 1b | Single "S,S" enantiomer of tetrabenazine | S | S | (structure shown with S at 11a and S at 3) |
| 1c | Tetrabenazine racemic mixture | R/S | R/S | (two structures shown: one with R at 11a and R at 3; another with S at 11a and S at 3) |
| 1d | Tetrabenazine & tetrabenazine compound in diasteromeric mixture | R | R/S | (two structures shown: one with R at 11a and R at 3; another with R at 11a and S at 3) |

*RP-3 = Ring position-3, RP-12 = Ring position-12

The examples given in Table 1 are merely illustrative of tetrabenazine compounds generally, and should not be construed to limit the scope of the invention. Entry 1d depicts a diastereomeric mixture comprising tetrabenazine XVII and a diastereomer having the same absolute stereochemistry at ring position-12 (R configuration) but having the opposite absolute stereochemistry at ring position-3 (S configuration).

As will be appreciated by those skilled in the art, a tetrabenazine compound comprising racemic tetrabenazine and diastereomers associated with each of the enantiomers of the racemate are also possible.

As noted, in one embodiment, the method of the present invention comprises reacting a nucleophilic alkenyl species with an aldehyde compound having structure II

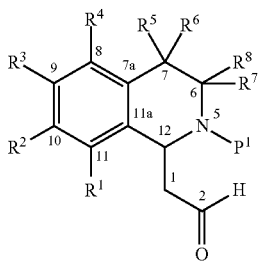

II wherein $R^1$-$R^4$ are independently hydrogen or an isotope thereof, a halogen atom, a $C_1$-$C_{20}$ aliphatic radical, a $C_2$-$C_{20}$ cycloaliphatic radical, or a $C_2$-$C_{20}$ aromatic radical, wherein at least one of $R^1$-$R^4$ is not hydrogen; $R^5$-$R^8$ are independently hydrogen or an isotope thereof, a $C_1$-$C_{20}$ aliphatic radical, a $C_2$-$C_{20}$ cycloaliphatic radical, or a $C_2$-$C_{20}$ aromatic radical; and $P^1$ is a protecting group.

Representative aldehyde compounds encompassed by generic formula II are illustrated in Table 2. The preparation of the aldehyde compound featured in Entry 2a of Table 2 is described in the experimental section of this disclosure. In general, the class of aldehyde compounds represented by structure II may be prepared by art recognized methods, for example using the methodology depicted in Scheme 1.

TABLE 2

Aldehyde Compounds Encompassed By Generic Structure II

| Entry | Compound Type | Ring Position* Stereo-chemistry | Structure |
|---|---|---|---|
| 2a | Single "R" enantiomer, "Boc" protecting group $P^1$ | RP-12 "R" | 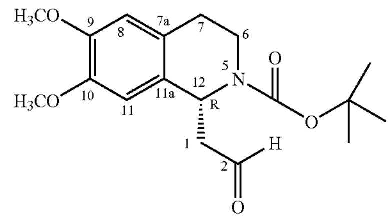 |
| 2b | Single "S" enantiomer, "Boc" protecting group $P^1$ | RP-12 "S" | 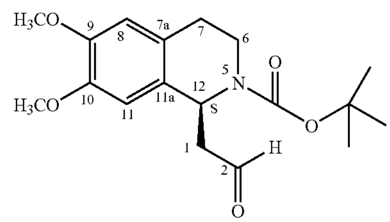 |
| 2c | Enantiomerically enriched mixture of "R" and "S" enantiomers, "alloc" protecting group $P^1$ | RP-12 "R/S" | |
| 2d | Racemic mixture of "R" and "S" enantiomers; "Fmoc" protecting group $P^1$ | RP-12 "R/S" | 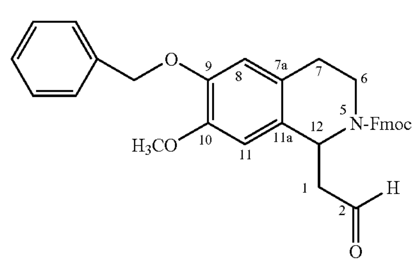 |

TABLE 2-continued

Aldehyde Compounds Encompassed By Generic Structure II

| Entry | Compound Type | Ring Position* Stereochemistry | Structure |
|---|---|---|---|
| 2e | Racemic mixture of "R" and "S" enantiomers; "Cbz" protecting group P¹ | RP-12 "R/S" | (structure) |
| 2f | Racemic mixture of "R" and "S" enantiomers; "Teoc" protecting group P¹ | RP-12 "R/S" | (structure) |
| 2g | Single "R,S" enantiomer, "Boc" protecting group P¹ | RP-12 "R", RP-6 "S" | (structure) |

RP-12 = Ring position-12, RP-6 = Ring position-6

In Scheme 1 the groups $R^1$-$R^8$ are defined as in generic structure II. DiBAlH represents the reductant diisobutyl aluminum hydride, and $(Boc)_2O$ represents di-tert-butyl dicarbonate (Boc anhydride). Thus, a phenethyl amine may be reacted with a malonate ester mono acid chloride to provide an amide which undergoes cyclization to a dihydroisoquinoline in the presence of phosphorous pentoxide ($P_2O_5$). Catalytic reduction of the intermediate dihydroisoquinoline affords the tetrahydroisoquinoline ester which is reduced to the corresponding aldehyde compound with diisobutylaluminium hydride. Treatment of the tetrahydroquinoline aldehyde with $(Boc)_2O$ affords aldehyde compound II wherein protecting group P¹ is a Boc group.

Scheme 1

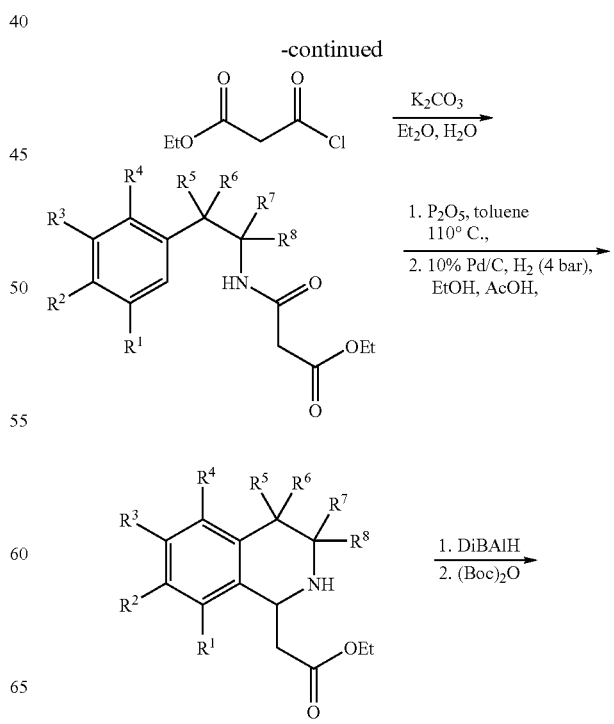

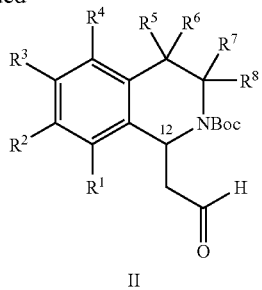

Aldehyde compounds II may also be prepared from intermediates prepared using methodology described by Sasamoto et al. (Journal of the American Chemical Society 128, 14010-14011, 2006). Sasamoto et al. disclose the preparation of enantiomerically enriched tetrahydroquinoline malonate compounds which may be converted to aldehyde compound II by selective hydrolysis of one of the ester moieties and decarboxylation followed by reduction of the resultant tetrahydroisoquinoline monoester to aldehyde compound II as depicted in Scheme 2. One of ordinary skill in the art will appreciate that the 2 mole percent DM-SEGPHOS represents a chiral catalyst responsible for the enantiomeric enrichment of the product aldehyde, and further that the use DM-SEGPHOS of opposite chirality as the chiral catalyst will afford a product aldehyde II enantiomerically enriched in the "S" enantiomer (aldehyde compound II having the S configuration at ring position-12. Suitable chiral catalysts include those disclosed by Sasamoto et al. (Journal of the American Chemical Society 128, 14010-14011, 2006), for example (S)-Binap, (R)-Binap, (S)-DM-Binap, (R)-DM-Binap, (S)-DM-SEGPHOS, (R)-DM-SEGPHOS. Typically use of a catalyst consisting of a ligand possessing a single, for example "S", configuration produces stereochemically enriched malonate adducts of the opposite "R" configuration and vice versa. In addition to the use of a chiral catalyst to generate aldehyde compounds II enriched in a single configuration at ring position-12, there are available a wide variety of methods for the separation of racemic aldehyde II into its constituent enantiomers. For example, racemic aldehyde compound II may be separated into its constituent enantiomers by high performance liquid chromatography (hplc) on a chiral hplc column. Other methods include conversion of the racemic TBZ compound into an adduct of the TBZ compound comprising a mixture of diastereomers separable by fractional crystallization. For example a racemic TBZ compound having structure I is first reacted with (−)-tartaric acid to form an adduct (ammonium tartarate salt) of the racemic TBZ compound comprising a mixture of diastereomers separable by fractional crystallization.

Those skilled in the art will appreciate that aldehyde compound shown in Scheme 1 is a mixture of "R" and "S" configurations at ring position 12, and that the aldehyde compound depicted in Scheme 2 represents a compound having the "R" configuration at ring position-12, and that both compounds fall within the scope of the genus defined by structure II.

In one embodiment, the product of the reaction of a nucleophilic alkenyl species with aldehyde compound II is an allylic alcohol which is oxidized to provide a first intermediate having structure III. Representative first intermediate compounds encompassed by generic structure III are illustrated in Table 3.

TABLE 3

First Intermediate Compounds Having Structure III

| Entry | Compound Type | Ring Position* Stereochemistry | Structure |
|---|---|---|---|
| 3a | Single "R" enantiomer, "Boc" protecting group $P^1$ | RP-12 "R" | 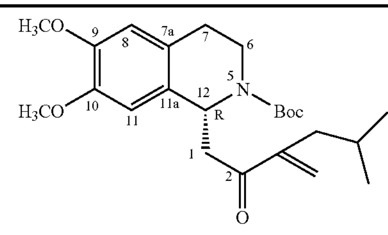 |

TABLE 3-continued

First Intermediate Compounds Having Structure III

| Entry | Compound Type | Ring Position* Stereo-chemistry | Structure |
|---|---|---|---|
| 3b | Single "S" enantiomer, "Boc" protecting group P¹ | RP-12 "S" | 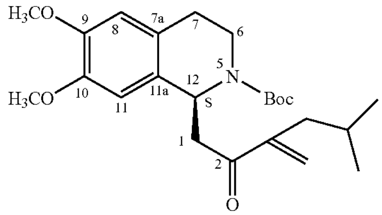 |
| 3c | Enantiomerically enriched mixture of "R" and "S" enantiomers, "alloc" protecting group P¹ | RP-12 "R/S" | |
| 3d | Racemic mixture of "R" and "S" enantiomers; "Fmoc" protecting group P¹ | RP-12 "R/S" | 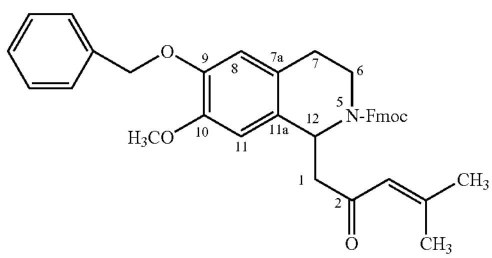 |
| 3e | Racemic mixture of "R" and "S" enantiomers; "Cbz" protecting group P¹ | RP-12 "R/S" | 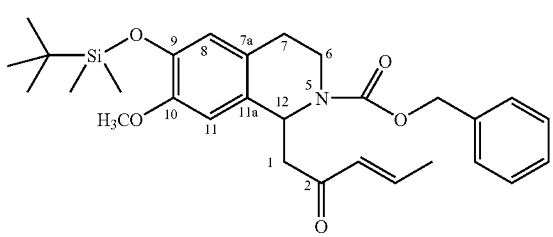 |
| 3f | Racemic mixture of "R" and "S" enantiomers; "Teoc" protecting group P¹ | RP-12 "R/S" | 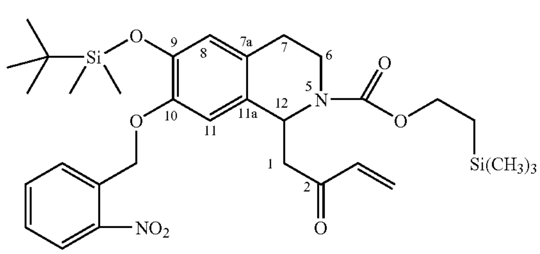 |

TABLE 3-continued

First Intermediate Compounds Having Structure III

| Entry | Compound Type | Ring Position* Stereo-chemistry | Structure |
|---|---|---|---|
| 3g | Single "R,S" enantiomer, "Boc" protecting group $P^1$ | RP-12 "R", RP-6 "S" | (structure with OCH₃ at positions 8,11; N-Boc; 2,4-difluorophenyl group; R at 11a, S at 6; numbered positions 1,2,5,6,7,7a,8,9,10,11,11a,12) |

RP-12 = Ring position-12, RP-6 = Ring position-6

As will be appreciated by one of ordinary skill in the art the allylic alcohol resulting from the addition of the nucleophilic alkenyl species to aldehyde compound II may be oxidized to provide the first intermediate using one or more of a variety of oxidizing reagents. In one embodiment, the allylic alcohol is oxidized using an oxidizing reagent (oxidant) selected from the group consisting of manganese oxide, Dess-Martin Reagent, pyridinium chlorochromate, Cornforth Reagent (pyridinium dichromate), chlorosulfonium chloride, Jones Reagent (chromic acid), Swern Oxidation reagent (DMSO-oxalyl chloride), Moffatt Oxidation reagent (DCC, DMSO under acidic conditions), von Doering Oxidation reagent (pyridine-$SO_3$), Corey-Kim Oxidation reagent (N-bromosuccinimide-dimethyl sulfide), Oppenhauer Oxidation reagent (acetone-aluminum isopropoxide), tetrapropylammonium peruthinate (TPAP), catalytic TEMPO oxidation in the presence of sodium hypochlorite solution. In one embodiment, the allylic alcohol is oxidized to the first intermediate using the Dess-Martin reagent.

There is no particular limitation on the nucleophilic alkenyl species other than that it react with aldehyde compound II to afford an allylic alcohol which upon oxidation affords first intermediate III. In one embodiment, the nucleophilic alkenyl species is a vinyl anion, for example vinyl lithium or vinyl magnesium bromide. In certain embodiments the nucleophilic alkenyl species is generated in situ from an alkenyl halide. For example, nucleophilic alkenyl species may generated in situ and induced to add to the carbonyl group of aldehyde compound II using Nozaki-Hiyama-Kishi ("NHK") reaction chemistry, nickel catalyzed formation of a nucleophilic organochromium reagent from, for example, an alkenyl halide. NHK reaction chemistry, is well suited for use within the context of the present invention and has been reviewed by Fürstner in *Chem. Rev.* 1999, 99, 991-1045 which review article is incorporated herein by reference in its entirety. Thus, in one embodiment the nucleophilic alkenyl species is generated using NHK reaction chemistry. Under such conditions the nucleophilic alkenyl species may be said to be prepared in the course of an NHK coupling reaction. In an alternate embodiment, the nucleophilic alkenyl species is derived from an alkenyl halide via metal halide exchange, for example lithiation, or Grignard reagent formation.

In one embodiment, the nucleophilic alkenyl species is derived from an alkenyl iodide having structure IV $$\text{IV}$$

(structure showing alkenyl iodide with $R^{11}$, $R^9$, $R^{10}$ substituents and I)

wherein $R^9$-$R^{11}$ are independently hydrogen or an isotope thereof, a $C_1$-$C_{20}$ aliphatic radical, a $C_2$-$C_{20}$ cycloaliphatic radical, or a $C_2$-$C_{20}$ aromatic radical. Alkenyl iodides having structure IV are suitable for use in Nozaki-Hiyama-Kishi ("NHK") reactions.

Representative alkenyl iodides having structure IV encompassed by generic structure IV are illustrated in Table 4.

TABLE 4

Alkenyl Iodides Having Structure IV

| Entry | $R^9$ | $R^{10}$ | $R^{11}$ |
|---|---|---|---|
| 4a | H | H | $CH_3$-CH-$CH_3$ (isopropyl) |
| 4b | H | H | H |
| 4c | $CH_3$ | $CH_3$ | H |
| 4d | $CH_3$ | H | H |
| 4e | 2,4-difluorophenyl | H | H |

In various embodiments of the present invention the protecting group $P^1$ of the first intermediate III is removed and thereafter an amino cyclization reaction is caused to occur (induced) thereby providing a product TBZ compound having structure I. In one embodiment, the amino cyclization reaction occurs spontaneously during the deprotection step under acidic conditions. In alternate embodiment, the amino cyclization reaction occurs spontaneously during the deprotection step under basic conditions.

In one embodiment, the protecting group $P^1$ is removed in a separate step following isolation and purification of first intermediate III. In alternate embodiment, the protecting group $P^1$ is removed as part of the oxidation step. Protecting groups $P^1$ are illustrated in Tables 2 and 3 and elsewhere in this disclosure. In general, the protecting group $P^1$ is a group that can be removed under relatively mild conditions without causing unintended transformation other sensitive structural features of the molecule. Sensitive structural features of the molecule include, for example, certain types functional groups (e.g. a methyl ether group at ring position-9 of tetrahydroisoquinoline III) and configuration/stereochemistry at particular positions within the molecule (e.g. "R" configuration at ring position-12 of tetrahydroisoquinoline III). Suitable protecting groups $P^1$ include Boc, Fmoc, Cbz, Alloc, Teoc, benzyl, and t-butyl groups, but do not include relatively stable groups such as n-alkyl groups (e.g. methyl, ethyl, and n-butyl). As is evident from the foregoing discussion, in one embodiment, the protecting group $P^1$ comprises a carbonyl group. In one embodiment, the protecting group $P^1$ is selected from the group consisting of Boc, Fmoc, Cbz, Alloc, Teoc, benzyl, and t-butyl groups. In one embodiment, the protecting group $P^1$ is the Boc group.

As noted, upon deprotection of first intermediate III, the deprotected first intermediate undergoes an amino cyclization reaction to provide a product TBZ compound having structure I. Depending on the structure of the first intermediate III, this amino cyclization reaction may take place at a rate at faster than the rate of deprotection (i.e. amino cyclization may take place at a rate which is faster than the rate of cleavage of the bond between the tetrahydroquinoline ring nitrogen and protecting group $P^1$). Under such conditions, the product of deprotection, in one embodiment structure III in which the protecting group $P^1$ has been replaced by hydrogen, is typically not isolable but is directly converted to TBZ compound I. In alternate embodiment, the amino cyclization reaction may take place at a rate which is slower than the rate of deprotection. Under such conditions, the product of deprotection, in one embodiment structure III in which the protecting group $P^1$ has been replaced by hydrogen, may be isolated, purified and subjected to the amino cyclization reaction in a separate step to afford the TBZ compound I.

As one of ordinary skill in the art will appreciate, the method of the present invention may be used to prepare compounds derived from TBZ compounds encompassed by generic structure I. Thus, in one embodiment, the method of the present invention further comprises a step of transforming the TBZ compound I into a product which may or may not be encompassed by structure I. For example, epimerization (inversion of stereochemistry) at ring position-3 results in a further elaborated product encompassed by structure I. One of ordinary skill in the art will recognize that reactions which transform the carbonyl group of TBZ compound I will result in further elaborated products not encompassed by structure I. The method of the present invention thus contemplates additional process steps which transform the TBZ compound having structure I provided by the method of the present invention.

In one embodiment, the method of the present invention further comprises a step of transforming the carbonyl group of the product TBZ compound I. In one embodiment, the method of the present invention further comprises a step of reducing the carbonyl group of TBZ compound I to the corresponding dihydro-TBZ compound (DTBZ compound), i.e. a compound wherein the ketone moiety of the TBZ compound has been reduced to a secondary alcohol. In one embodiment, the method of the present invention provides a DTBZ compound which is a mixture of diastereomers. In another embodiment, the method of the present invention provides a DTBZ compound which is a single diastereomer.

In another embodiment, the present invention provides a method of preparing a TBZ compound having structure V,

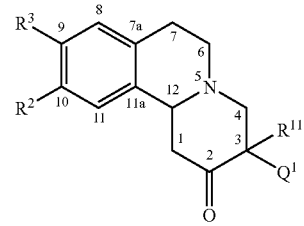

V said method comprising:
(a) reacting a nucleophilic alkenyl species with aldehyde compound VI

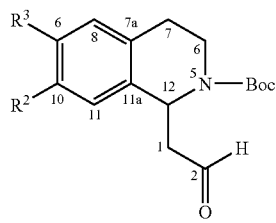

VI and oxidizing of the resultant allylic alcohol to provide a first intermediate having structure VII; and

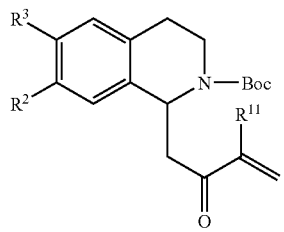

VII (b) removing the Boc protecting group and inducing an amino cyclization reaction to provide a product TBZ compound having structure V, wherein with respect to structures V, VI, and VII; $R^2$-$R^3$ are independently hydrogen or an isotope thereof, a halogen atom, a $C_1$-$C_{20}$ aliphatic radical, a $C_2$-$C_{20}$ cycloaliphatic radical, or a $C_2$-$C_{20}$ aromatic radical, wherein at least one of $R^2$-$R^3$ is not hydrogen; and $R^{11}$ is hydrogen or an isotope thereof, a $C_1$-$C_{20}$ aliphatic radical, a $C_2$-$C_{20}$ cycloaliphatic radical, or a $C_2$-$C_{20}$ aromatic radical.

Representative TBZ compounds encompassed by generic formula V are illustrated in Table 5.

TABLE 5
Exemplary TBZ Compounds Encompassed By Generic Formula V
| Entry | R² | R³ | R¹¹ | Q¹ | Structure |
|---|---|---|---|---|---|
| 5a | EtO | EtO | Iso-butyl | H | 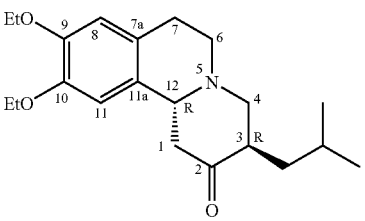 |
| 5b | EtO | EtO | Iso-butyl | H | 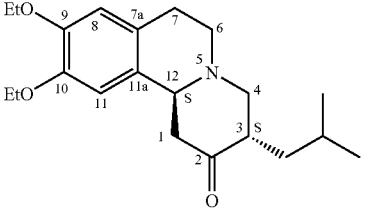 |
| 5c | H | CF₃ | n-butyl | D | 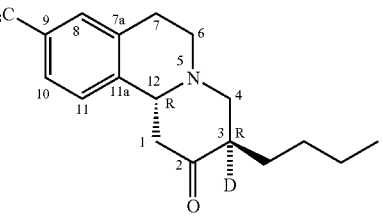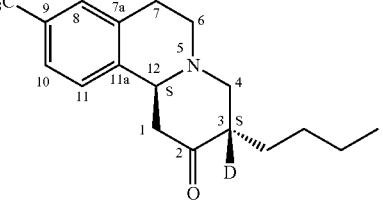 |
| 5d | O-benzyl | CH₃O | Propyl | H | 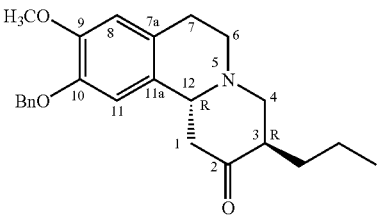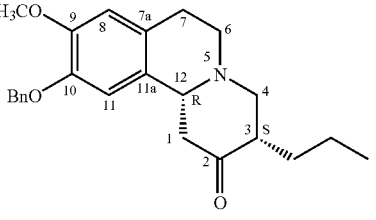 |

Representative aldehyde compounds encompassed by generic formula VIII are illustrated in Table 6.

TABLE 6

Exemplary Aldehyde Compounds Encompassed by Generic Structure VI

| Entry | R² | R³ | Structure |
|---|---|---|---|
| 6a | t-Bu(Me)₂Si | CH₃O | 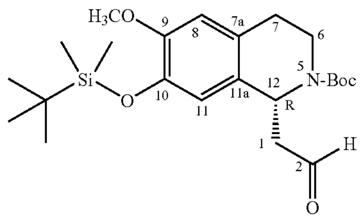 |
| 6b | CH₃O | t-Bu(Me)₂Si | 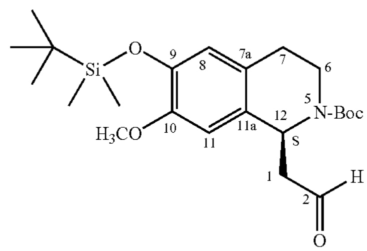 |
| 6c | CH₃O | CH₃O | 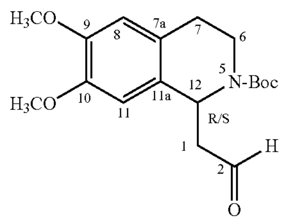 |
| 6d | CH₃O | O-benzyl | 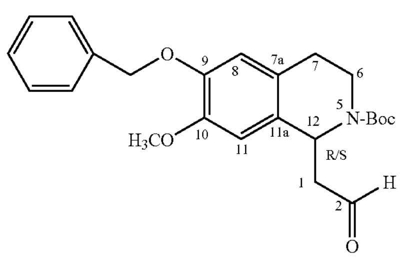 |

Representative first intermediate compounds encompassed by generic structure VII are illustrated in Table 7.

TABLE 7

Exemplary First Intermediate Compounds Encompassed by Generic Structure VII

| Entry | R² | R³ | R¹¹ | Structure |
|---|---|---|---|---|
| 7a | t-Bu(Me)₂Si | CH₃O | H | 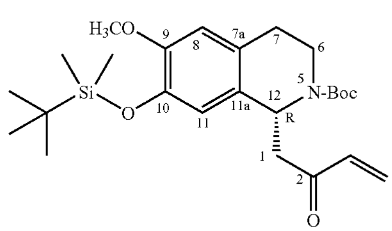 |

TABLE 7-continued

Exemplary First Intermediate Compounds Encompassed by Generic Structure VII

| Entry | $R^2$ | $R^3$ | $R^{11}$ | Structure |
|---|---|---|---|---|
| 7b | $CH_3S$ | $t\text{-}Bu(Me)_2Si$ | $CH_3$ | 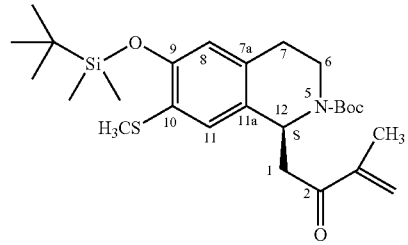 |
| 7c | $CH_3O$ | F | isobutyl | 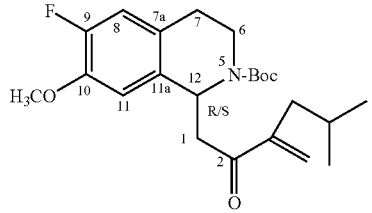 |
| 7d | $CH_3O$ | O-benzyl | n-propyl | 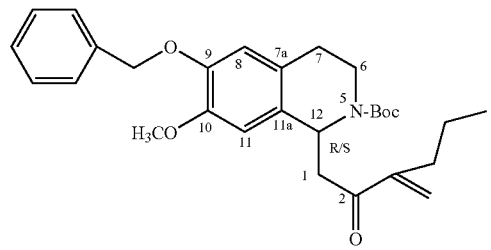 |

In another embodiment, the present invention provides a method of preparing an enantiomerically enriched TBZ compound comprising at least 95 mole percent enantiomer VIII,

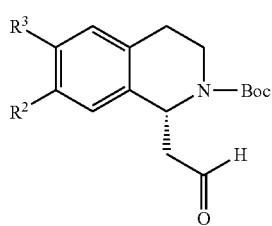

VIII said method comprising:

(a) reacting a nucleophilic alkenyl species with an aldehyde compound comprising at least 95 mole percent enantiomer IX

IX and oxidizing the resultant allylic alcohol to provide a first intermediate having structure X; and

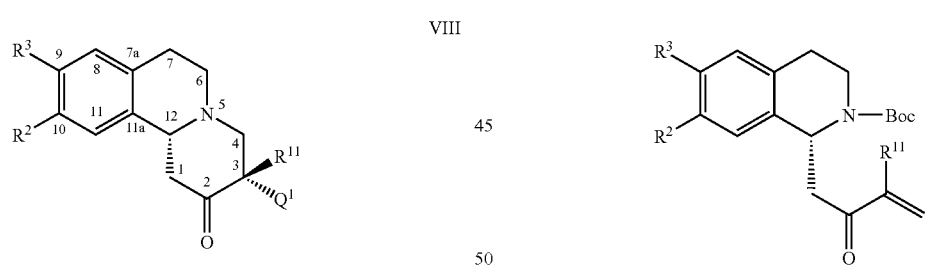

X (b) removing the Boc protecting group and inducing an amino cyclization reaction to provide a product TBZ compound having structure VIII, wherein with respect to structures VIII, IX, and X; $R^2$-$R^3$ are independently hydrogen or an isotope thereof, a halogen atom, a $C_1$-$C_{20}$ aliphatic radical, a $C_2$-$C_{20}$ cycloaliphatic radical, or a $C_2$-$C_{20}$ aromatic radical, wherein at least one of $R^2$-$R^3$ is not hydrogen; $R^{11}$ is hydrogen or an isotope thereof, a $C_1$-$C_{20}$ aliphatic radical, a $C_2$-$C_{20}$ cycloaliphatic radical, or a $C_2$-$C_{20}$ aromatic radical; and $Q^1$ is hydrogen or an isotope thereof.

Representative TBZ compounds encompassed by generic formula VIII are illustrated in Table 8.

TABLE 8

Exemplary TBZ Compounds Encompassed By Generic Formula VIII

| Entry | $R^2$ | $R^3$ | $R^{11}$ | $Q^1$ | Structure |
|---|---|---|---|---|---|
| 8a | H | EtO | Iso-butyl | H | 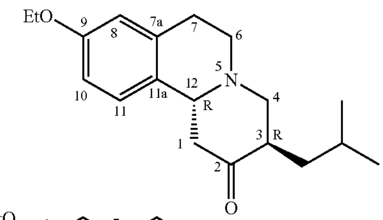 |
| 8b | EtO | EtO | 2,2-dimethyl pentyl | H | 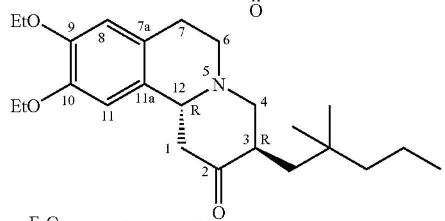 |
| 8c | H | $CF_3$ | n-butyl | D | 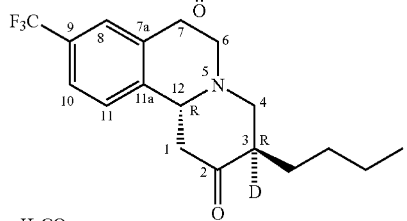 |
| 8d | O-benzyl | $CH_3O$ | Propyl | D | 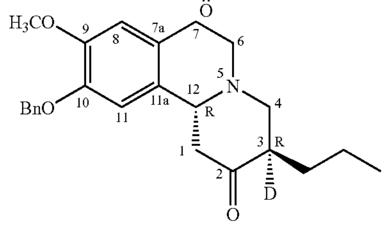 |

Representative aldehyde compounds encompassed by generic formula IX are illustrated in Table 9.

TABLE 9

Exemplary Aldehyde Compounds Encompassed By Generic Structure IX

| Entry | $R^2$ | $R^3$ | Structure |
|---|---|---|---|
| 9a | H | EtO | 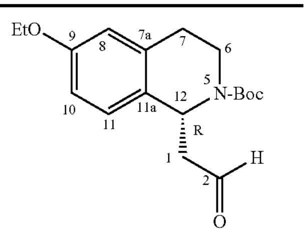 |
| 9b | EtO | EtO | 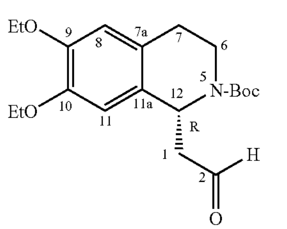 |
| 9c | O-butyl | $CF_3$ | |
| 9d | O-benzyl | $CH_3O$ | |

Representative first intermediate compounds encompassed by generic formula X are illustrated in Table 10.

TABLE 10

Exemplary First Intermediate Compounds Encompassed By Generic Structure X

| Entry | $R^2$ | $R^3$ | $R^{11}$ | Structure |
|---|---|---|---|---|
| 10a | H | EtO | Iso-butyl | 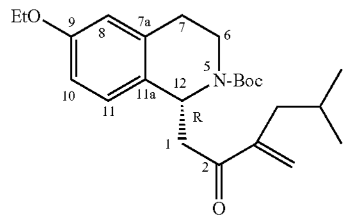 |
| 10b | EtO | EtO | 2,2-dimethyl pentyl | 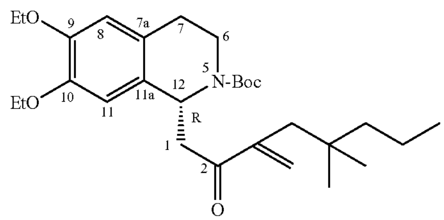 |
| 10c | O-butyl | $CF_3$ | n-butyl | 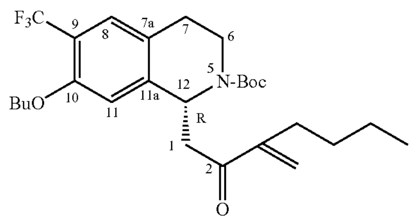 |
| 10d | O-benzyl | CF3 | Propyl | 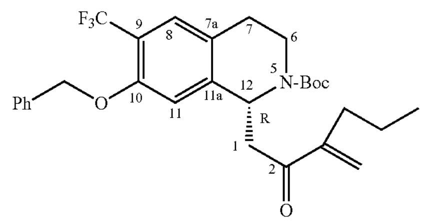 |

As noted, conversion of first intermediate III to TBZ compound I is effected by removal of the protecting group $P^1$ and inducing an amino cyclization reaction. Techniques for the removal of protecting groups $P^1$ are well known to one of ordinary skill in the art and include, for example, the acid catalyzed removal of a Boc protecting group $P^1$ as disclosed in the Examples section herein, photolysis of an o-nitrobenzyl protecting group $P^1$, and hydrogenolysis of a benzyl protecting group $P^1$. Removal of the protecting group $P^1$ from the first intermediate III results in the formation of a deprotected first intermediate having structure XI

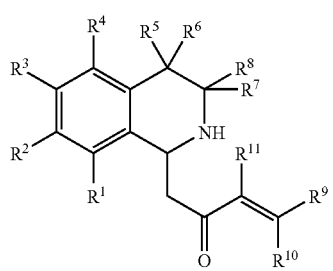

wherein $R^1$-$R^4$ are independently hydrogen or an isotope thereof, a halogen atom, a $C_1$-$C_{20}$ aliphatic radical, a $C_2$-$C_{20}$ cycloaliphatic radical, or a $C_2$-$C_{20}$ aromatic radical, wherein at least one of $R^1$-$R^4$ is not hydrogen; and $R^5$-$R^{11}$ are independently hydrogen or an isotope thereof, a $C_1$-$C_{20}$ aliphatic radical, a $C_2$-$C_{20}$ cycloaliphatic radical, or a $C_2$-$C_{20}$ aromatic radical.

Representative deprotected first intermediate compounds encompassed by generic formula XI are illustrated in Table 11.

TABLE 11

Exemplary Deprotected First Intermediate Compounds XI

| Entry | Compound Type | Ring Position* Stereo-chemistry | Structure |
|---|---|---|---|
| 11a | Single "R" enantiomer | RP-12 "R" | 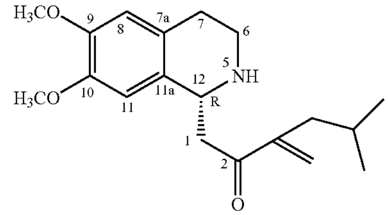 |
| 11b | Single "S" enantiomer | RP-12 "S" | 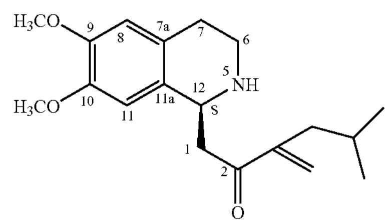 |
| 11c | Enantiomerically enriched mixture of "R" and "S" enantiomers | RP-12 "R/S" | 95% / 5% |
| 11d | Racemic mixture of "R" and "S" enantiomers | RP-12 "R/S" | 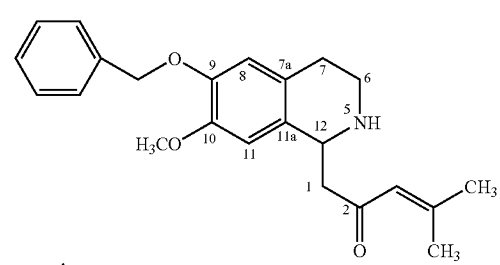 |
| 11e | Racemic mixture of "R" and "S" enantiomers | RP-12 "R/S" | 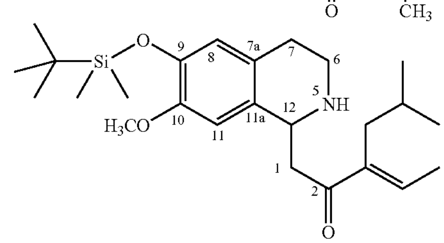 |

TABLE 11-continued

Exemplary Deprotected First Intermediate Compounds XI

| Entry | Compound Type | Ring Position* Stereo-chemistry | Structure |
|---|---|---|---|
| 11f | Racemic mixture of "R" and "S" enantiomers | RP-12 "R/S" | 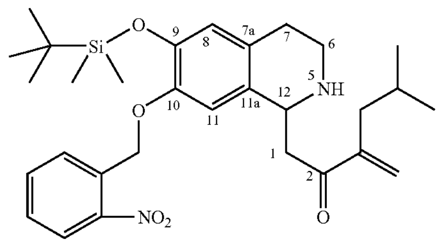 |
| 11g | Single "R,S" enantiomer | RP-12 "R" RP-6 "S" | 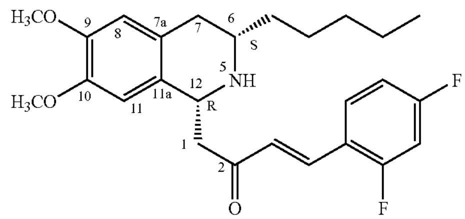 |

RP-12 = Ring position-12, RP-6 = Ring position-6

As discussed herein, the method of the present invention comprises a step in which an nucleophilic alkenyl species is reacted with aldehyde compound II which results in the formation of an allylic alcohol which is oxidized to a first intermediate having structure III. The allylic alcohol is itself a valuable intermediate and is, in certain embodiments, isolable. In general, the allylic alcohol precursor to first intermediate III has structure XII

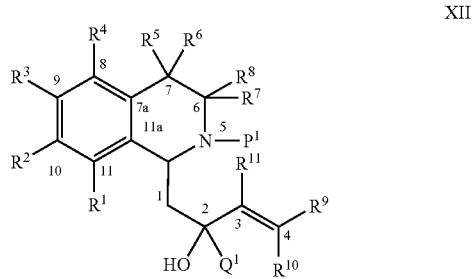

XII wherein $R^1$-$R^4$ are independently hydrogen or an isotope thereof, a halogen atom, a $C_1$-$C_{20}$ aliphatic radical, a $C_2$-$C_{20}$ cycloaliphatic radical, or a $C_2$-$C_{20}$ aromatic radical, wherein at least one of $R^1$-$R^4$ is not hydrogen; $R^5$-$R^{11}$ are independently hydrogen or an isotope thereof, a $C_1$-$C_{20}$ aliphatic radical, a $C_2$-$C_{20}$ cycloaliphatic radical, or a $C_2$-$C_{20}$ aromatic radical; $P^1$ is a protecting group, and $Q^1$ is hydrogen or an isotope thereof.

Representative allylic alcohol compounds encompassed by generic formula XII are illustrated in Table 12.

TABLE 12

Exemplary Allylic Alcohol Compounds XII

| Entry | Compound Type | Ring Position* Stereo-chemistry | Structure |
|---|---|---|---|
| 12a | Single "R,S" enantiomer | RP-12 "R", RP-2 "S" | 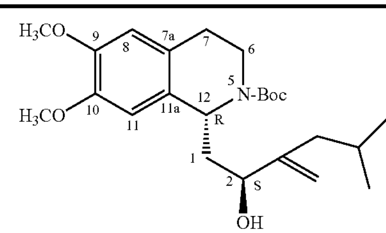 |

TABLE 12-continued

Exemplary Allylic Alcohol Compounds XII

| Entry | Compound Type | Ring Position* Stereo-chemistry | Structure |
|---|---|---|---|
| 12b | Single "S,R" enantiomer | RP-12 "S", RP-2 "R" | 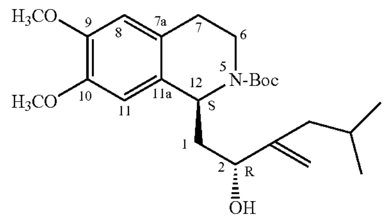 |
| 12c | Enantiomerically enriched mixture of "R" and "S" enantiomers, epimeric at RP-2 | RP-12 "R/S", RP-2 "R/S" | |
| 12d | Racemic mixture of "R" and "S" enantiomers, epimeric at RP-2 | RP-12 "R/S", RP-2 "R/S" | 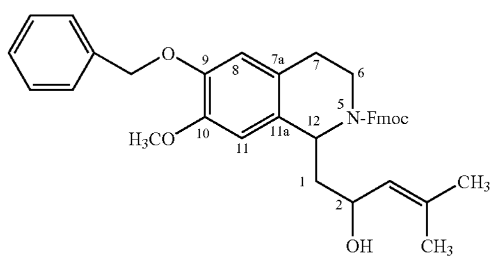 |
| 12e | Racemic mixture of "R" and "S" enantiomers, epimeric at RP-2 | RP-12 "R/S", RP-2 "R/S" | 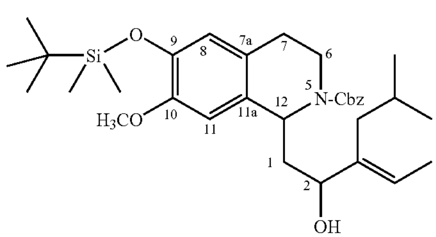 |
| 12f | Racemic mixture of "R" and "S" enantiomers, epimeric at RP-2 | RP-12 "R/S", RP-2 "R/S" | 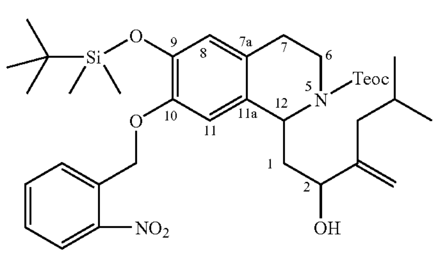 |

TABLE 12-continued

Exemplary Allylic Alcohol Compounds XII

| Entry | Compound Type | Ring Position* Stereo-chemistry | Structure |
|---|---|---|---|
| 12g | Single "R,S,S" enantiomer | RP-12 "R", RP-6 "S", RP-2 "S" | (structure shown) |

In one embodiment, the present invention provides a deprotected allylic alcohol compound having structure XIII

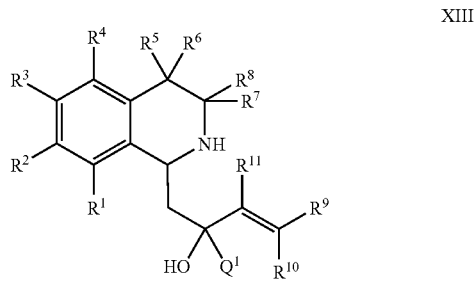

XIII wherein $R^1$-$R^4$ are independently hydrogen or an isotope thereof, a halogen atom, a $C_1$-$C_{20}$ aliphatic radical, a $C_2$-$C_{20}$ cycloaliphatic radical, or a $C_2$-$C_{20}$ aromatic radical, wherein at least one of $R^1$-$R^4$ is not hydrogen; $R^5$-$R^{11}$ are independently hydrogen or an isotope thereof, a $C_1$-$C_{20}$ aliphatic radical, a $C_2$-$C_{20}$ cycloaliphatic radical, or a $C_2$-$C_{20}$ aromatic radical; and $Q^1$ is hydrogen or an isotope thereof.

Deprotected allylic alcohol compound XIII is typically derived from allylic alcohol compound XII. One of ordinary skill in the art will recognize that compound XIII is identical to compound XII except that the protecting group $P^1$ of compound XII has been removed and is replaced by a hydrogen atom in compound XIII. Allylic alcohol compound XIII is thus referred to as a "deprotected allylic alcohol". Deprotection of allylic alcohol XII may be effected by a variety of methods known to those skilled in the art, including those methods used to effect deprotection of first intermediate III, as disclosed herein. In one aspect, the deprotected allylic alcohol compounds XIII provided by the present invention are useful in the preparation of TBZ compounds. Thus, oxidation of deprotected allylic alcohol XIII with the Dess-Martin reagent may provide the TBZ compound I in a process believed to involve formation of a deprotected first intermediate having structure XI followed by an amino cyclization reaction to afford TBZ compound I.

Representative deprotected allylic alcohol compounds encompassed by generic formula XIII are illustrated in Table 13.

TABLE 13

Exemplary Deprotected Allylic Alcohol Compounds XIII

| Entry | Compound Type | Ring Position* Stereo-chemistry | Structure |
|---|---|---|---|
| 13a | Single "R,S" enantiomer | RP-12 "R", RP-2 "S" | (structure shown) |
| 13b | Single "S,R" enantiomer | RP-12 "S", RP-2 "R" | (structure shown) |

TABLE 13-continued

Exemplary Deprotected Allylic Alcohol Compounds XIII

| Entry | Compound Type | Ring Position* Stereo-chemistry | Structure |
|---|---|---|---|
| 13c | Enantiomerically enriched mixture of "R" and "S" enantiomers, epimeric at RP-2 | RP-12 "R/S", RP-2 "R/S" | 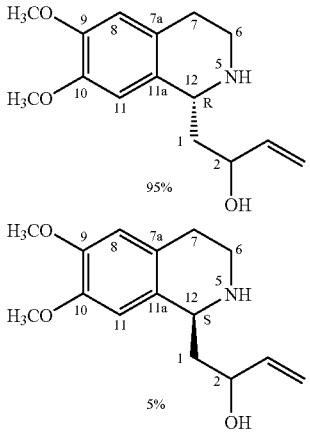 |
| 13d | Racemic mixture of "R" and "S" enantiomers, epimeric at RP-2 | RP-12 "R/S", RP-2 "R/S" | 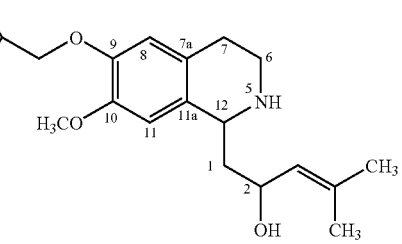 |
| 13e | Racemic mixture of "R" and "S" enantiomers, epimeric at RP-2 | RP-12 "R/S", RP-2 "R/S" | 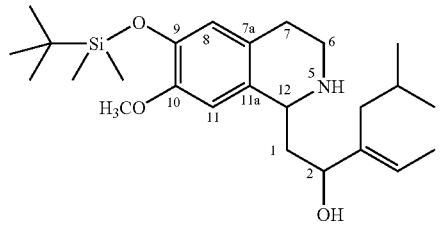 |
| 13f | Racemic mixture of "R" and "S" enantiomers, epimeric at RP-2 | RP-12 "R/S", RP-2 "R/S" | 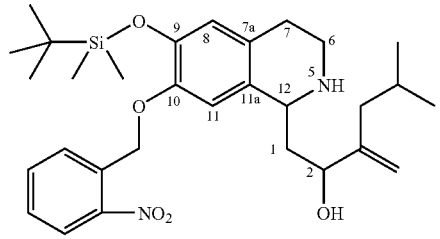 |
| 13g | Single "R,S,S" enantiomer | RP-12 "R", RP-6 "S", RP-2 "S" | 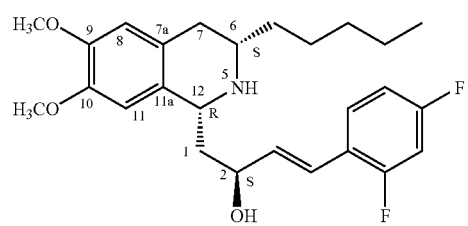 |

In one embodiment, the present invention provides a deprotected first intermediate having structure XIV

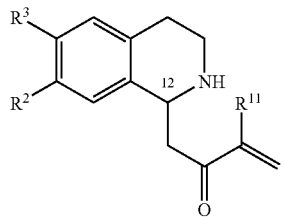

wherein $R^2$-$R^3$ are independently hydrogen or an isotope thereof, a halogen atom, a $C_1$-$C_{20}$ aliphatic radical, a $C_2$-$C_{20}$ cycloaliphatic radical, or a $C_2$-$C_{20}$ aromatic radical, wherein at least one of $R^2$-$R^3$ is not hydrogen; and $R^{11}$ is hydrogen or an isotope thereof, a $C_1$-$C_{20}$ aliphatic radical, a $C_2$-$C_{20}$ cycloaliphatic radical, or a $C_2$-$C_{20}$ aromatic radical.

Deprotected first intermediate XIV may be prepared by removing the protecting group $P^1$ in first intermediate VII. Removal of the protecting group $P^1$ in first intermediate VII can be effected by methods known to one of ordinary skill in the art. In addition, the present disclosure provides detailed guidance on the removal of protecting groups. Representative deprotected first intermediate compounds encompassed by generic formula XIV are given in Table 14.

TABLE 14

Exemplary Deprotected First Intermediate Compounds XIV

| Entry | $R^2$ | $R^3$ | $R^{11}$ | Structure |
|---|---|---|---|---|
| 14a | t-Bu(Me)$_2$Si | CH$_3$O | H | 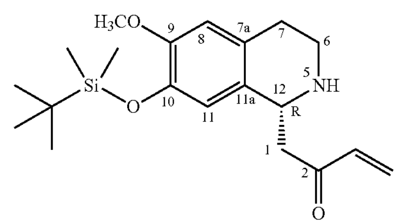 |
| 14b | CH$_3$S | t-Bu(Me)$_2$Si | CH$_3$ | 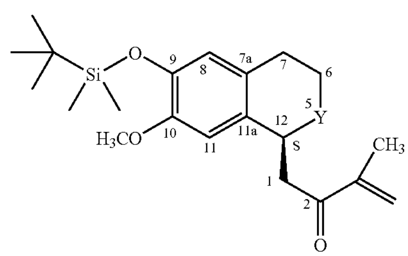 |
| 14c | CH$_3$O | F | isobutyl | 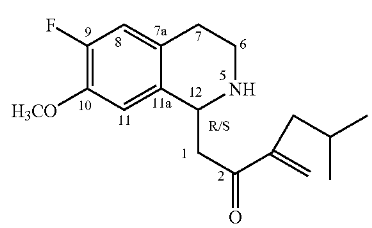 |
| 14d | CH$_3$O | O-benzyl | n-propyl | 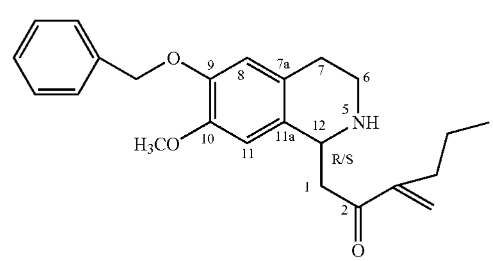 |

In one embodiment, the present invention provides a deprotected first intermediate having structure XV. One of ordinary skill in the art will appreciate that deprotected first intermediate having structure XV may be obtained from first intermediate X wherein each of $R^2$ and $R^3$ is the $C_1$ aliphatic radical, methoxy, and $R^{11}$ is the $C_4$ aliphatic radical, isobutyl, by removal of protecting group $P^1$. Removal of the protecting group $P^1$ in first intermediate X can be effected by methods known to one of ordinary skill in the art. In addition, the present disclosure provides detailed guidance on the removal of protecting groups. One of ordinary skill in the art will recognize that the deprotected first intermediate having structure XV represents a single enantiomer having the "R" configuration at ring position-12. In one embodiment, deprotected first intermediate XV is obtained essentially as a single enantiomer, for example a composition containing essentially a single component, that component being a single enantiomer. In another embodiment, deprotected first intermediate XV is obtained as a component 1 of a highly enantiomerically enriched composition comprising about 95 mole percent deprotected first intermediate XV together with about 5 mole percent of its optical antipode, deprotected first intermediate XVI. In another embodiment deprotected first intermediate XV is a component of a diastereomeric mixture. Although under a wide variety of conditions, deprotected first intermediate XV is rapidly converted via amino cyclization to (+)-tetrabenazine XVII, it nonetheless represents a highly valuable and useful composition of matter.

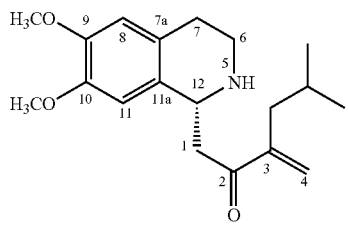

XV

In alternate embodiment, the present invention provides a deprotected first intermediate having structure XVI. One of ordinary skill in the art will appreciate that deprotected first intermediate having structure XVI may be obtained from first intermediate VII wherein the absolute stereochemistry at ring position-12 is "S", each of $R^2$ and $R^3$ is the $C_1$ aliphatic radical, methoxy, and $R^{11}$ is the $C_4$ aliphatic radical, isobutyl, by removal of protecting group $P^1$. Removal of the protecting group $P^1$ in first intermediate VII can be effected by methods known to one of ordinary skill in the art. In addition, the present disclosure provides detailed guidance on the removal of protecting groups. One of ordinary skill in the art will recognize that the deprotected first intermediate having structure XVI represents a single enantiomer having the "S" configuration at ring position-12. In one embodiment, deprotected first intermediate XVI is obtained essentially as a single enantiomer, e.g. a composition containing no component which is the mirror image of compound XVI. In another embodiment, deprotected first intermediate XVI is obtained as a component of a highly enantiomerically enriched composition comprising about 95 mole percent deprotected first intermediate XVI together with about 5 mole percent of its optical antipode, deprotected first intermediate XV. In another embodiment deprotected first intermediate XVI is a component of a diastereomeric mixture. Although under a wide variety of conditions, deprotected first intermediate XVI is rapidly converted via amino cyclization to (−)-tetrabenazine XVIII, it nonetheless represents a highly valuable and useful composition of matter.

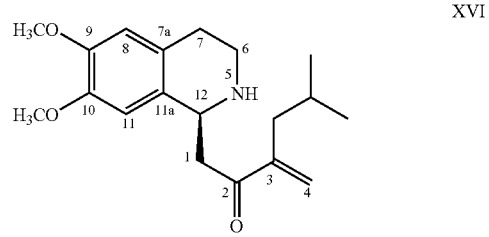

XVI

EXAMPLES

The following examples are intended only to illustrate methods and embodiments in accordance with the invention, and as such should not be construed as imposing limitations upon the claims.

Example 1

Preparation of Protected Diester 2

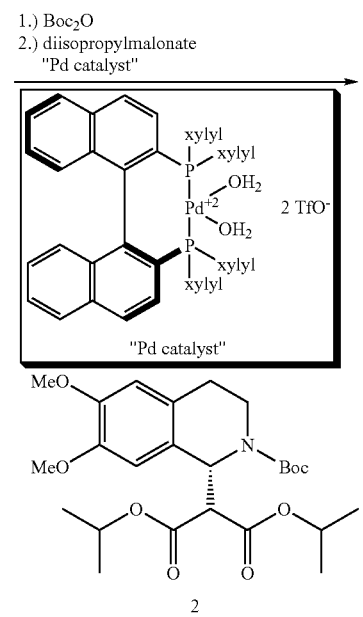

The dihydroisoquinoline 1 (1.0 eq.) and Boc anhydride (1.5 eq.) were dissolved in $CH_2Cl_2$ at room temperature to provide a 1.5 M solution with respect to the dihydroisoquinoline. The mixture was allowed to stir for 30 min. Following the allotted time, the reaction mixture was cooled to 0° C. and then diisopropylmalonate (1.5 eq.) followed by a pre-chilled solution of the Pd catalyst (0.008 eq.) in dichloromethane were added successively to the reaction mixture to provide a final reaction concentration of 0.84 M with respect to the starting dihydroisoquinoline. The reaction mixture was allowed to continue stirring at ~2.5° C. for 15 h. Following this time EtOAc and brine were added to the reaction mixture. The aqueous layer was extracted with three portions of EtOAc and the combined organic layers were dried (Na$_2$SO$_4$), filtered, and concentrated under reduced pressure to provide the crude product. The crude material was dissolved in a minimal amount of dichloromethane and purified by flash chromatography on SiO$_2$ (15-30% EtOAc-hexanes, elution was observed at 285 nm and 228 nm). The product 2 was a colorless solid that existed as a mixture of rotamers in solution at room temperature 94%: [α]$^{26}_D$ −69.0 (c 0.21, CHCl$_3$); $^1$H NMR (CDCl$_3$) δ 0.81-1.02 (m, 6H), 1.06-1.17 (m, 6H), 1.23-1.38 (m, 9H), 2.51-2.63 (m, 1H), 2.64-2.77 (m, 1H), 3.20-3.29 (m, 0.6H), 3.32-3.41 (m, 0.4H), 3.51-3.58 (m, 1H), 3.62-3.70 (m, 6H), 3.70-3.76 (m, 0.4H), 3.91-4.01 (m, 0.6H), 4.65-4.82 (m, 1H), 4.83-4.98 (m, 1H), 5.71 (apparent d, J=5.7 Hz, 0.6H), 5.78 (apparent d, J=7.9 Hz, 0.4H), 6.42-6.49 (m, 1H), 6.77 (s, 0.6H), 6.81 (s, 0.4H); $^{13}$C NMR (CDCl$_3$) δ 21.02, 21.09, 21.18, 21.32, 27.24, 27.95, 28.02, 37.60, 39.34, 52.11, 52.83, 55.48, 55.52, 59.28, 60.08, 68.58, 68.76, 68.82, 79.46, 80.03, 110.09, 110.73, 111.13, 126.11, 126.18, 126.37, 127.07, 146.81, 146.87, 147.93, 153.86, 154.30, 166.29, 166.78, 166.94, 167.06.

Example 2

Selective Hydrolysis and Decarboxylation of Protected Ester 3

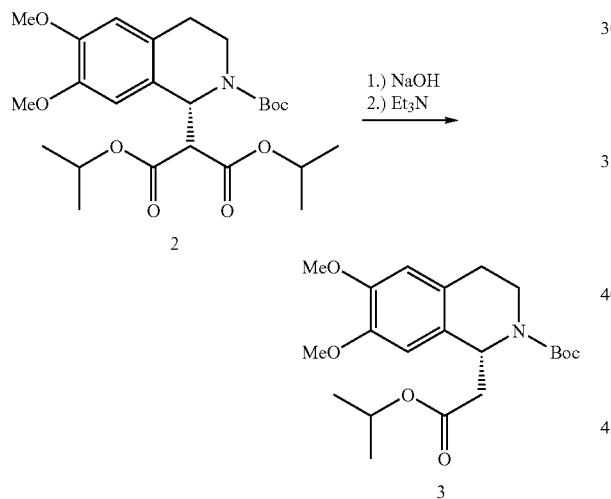

The starting material 2 was taken up in isopropanol to provide a 0.2 M solution of 2. To this solution was added 1M aqueous NaOH solution bringing the final concentration of the reaction mixture to 0.1M with respect to the malonate 2. The reaction mixture was heated to and maintained 70° C. for 22 min. (timing was started when the temperature of the reaction mixture temp exceeded 65° C.). Following the allotted time the reaction mixture was quickly cooled to 0° C. The reaction mixture carefully acidified with 2M aqueous HCl and extracted with three portions of dichloromethane. The combined organic extracts dried (Na$_2$SO$_4$), filtered and concentrated under reduced pressure. The isolated material was taken up in THF to provide a 0.1 M solution (based on the original quantity of 2 used in the reaction mixture) and triethylamine (1.0 eq) was added to the reaction mixture at room temperature. The reaction mixture was heated to its reflux temperature and maintained at this temperature for 90 min. The reaction mixture was concentrated under reduced pressure, dissolved in a minimal quantity of CH$_2$Cl$_2$ and was immediately purified by column chromatography on SiO$_2$ (15-40% EtOAc-hexanes; 40%, the eluant was monitored at 284 nm). The product 3 existed as a mixture of rotamers at room temperature and was a colorless foam 79%: [α]$^{26}_D$ −82 (c 0.24, CH$_2$Cl$_2$); $^1$H NMR (CDCl$_3$) δ 1.19-1.25 (m, 6H), 1.43-1.49 (m, 9H), 2.58-2.69 (m, 2H), 2.70-2.77 (m, 1H), 2.78-2.92 (m, 1H), 3.13-3.43 (m, 1H), 3.81-3.85 (m, 6H), 3.86-4.01 (m, 1H), 4.91-5.05 (m, 1H), 5.38-5.61 (m, 1H), 6.56-6.61 (m, 1H), 6.64-6.70 (s, 1H); $^{13}$C NMR (CDCl$_3$) δ 21.75, 21.90, 27.93, 28.08, 28.44, 37.53, 38.75, 42.22, 42.81, 51.11, 51.87, 55.92, 56.02, 68.08, 79.74, 80.21, 109.60, 109.99, 111.44, 111.54, 126.28, 126.48, 128.54, 128.76, 147.51, 147.97, 154.39, 154.51, 170.36, 170.59; LRMS-(ESI+) calcd for (C$_{21}$H$_{31}$NO$_6$+H) ([M+H]$^+$ 394.22. found 394.16.

Example 3

Preparation of Aldehyde Compound 4

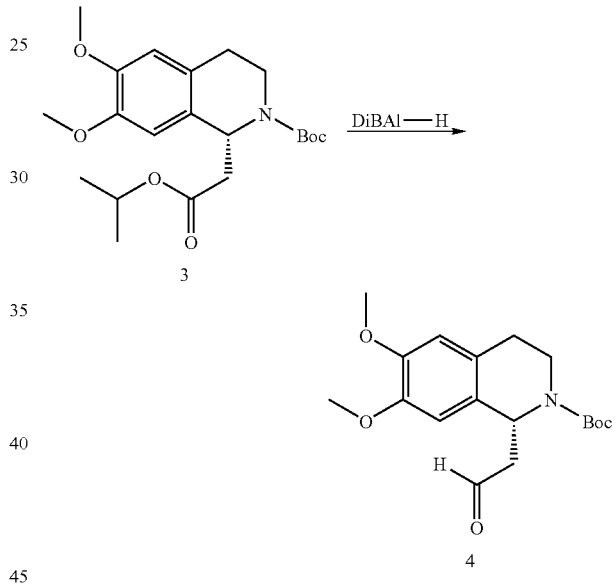

To a 0.12 M solution of the starting monoester (3, 1.0 eq.) in toluene at −78° C. was added a 1.5 M solution of DiBAl-H in hexanes (1.5 eq.) dropwise via a syringe pump. Following the addition the reaction mixture was stirred at −78° C. for 2 h. The reaction mixture was quenched by the addition of EtOAc and was then acidified with saturated aqueous citric acid solution. The reaction mixture was allowed to warm to room temperature and continue stirring for 30 min. The phases were separated, and the aqueous layer extracted with three portions of EtOAc. The combined organic extracts were washed with two portions of 2 M aqueous HCl solution, brine, dried (MgSO$_4$), filtered, and concentrated under reduced pressure. The crude product was subjected purification on SiO$_2$ (15-35% EtOAc-hexanes; Elution was observed at 285 nm and 228 nm). The isolated product aldehyde compound 4 was a colorless foam. The product existed as a 1:1 mixture of rotamers at room temperature 76%: [α]$^{26}_D$ −116 (c 0.26, CH$_2$Cl$_2$); $^1$H NMR (CDCl$_3$) δ 1.40 (s, 9H), 2.58 (apparent t, J=3.8 Hz, 0.5H), 2.61 (apparent t, J=3.5 Hz, 0.5H), 2.68-2.88 (m, 3H), 3.02-3.27 (m, 1H), 3.78 (apparent s, 6H), 3.87-3.99 (m, 0.5H), 4.08-4.23 (m, 0.5H), 5.37-5.68 (m, 1H), 6.55 (s, 1H), 6.58 (s, 1H), 9.78 (s, 1H); $^{13}$C NMR (CDCl$_3$) δ 20.90, 28.02, 28.27, 37.23, 38.65, 49.29, 49.93, 51.12, 55.83, 55.96, 80.13, 80.64, 109.42, 109.52, 111.52, 126.34, 126.51, 127.78, 127.82, 147.72, 147.97, 153.85, 154.62, 200.08, 200.33.

Example 4

Reaction of Aldehyde Compound 4 with Nucleophilic Alkenyl Species Derived from Alkenyl Iodide 5 with to Provide Allylic Alcohol 6

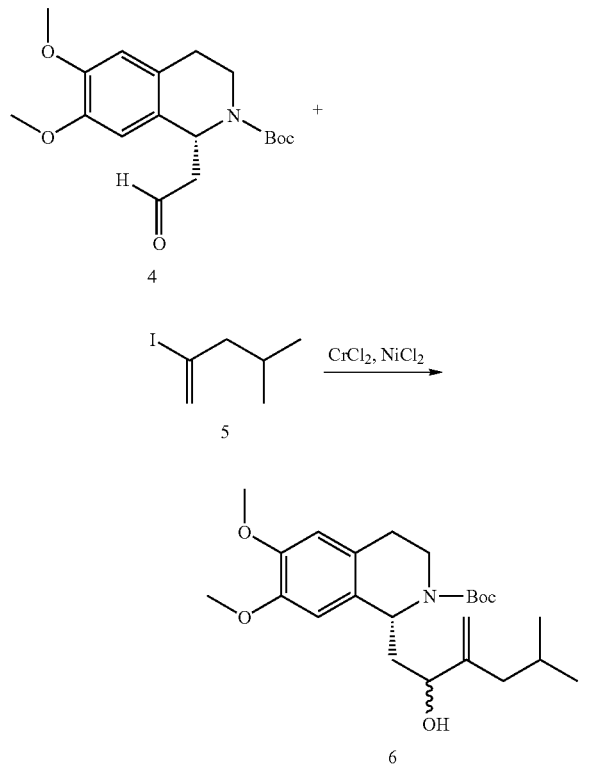

To a neat mixture of the alkenyl iodide 5 (1.0 eq) and the aldehyde compound 4 (1.0 eq.) at room temperature was added 2.65 eq. of chromium chloride doped with 0.5% NiCl$_2$ (w/w). The mixture was vortexed for about 2 min. to provide a homogeneous, green/grey paste and then stirred under nitrogen for an additional 10 min. after which time anhydrous DMF was added to bring the final reaction concentration to 0.36 M. The reaction mixture was deep green in color and was permitted to continue stirring at room temperature for 14 h. Following the allotted time, the reaction mixture was diluted with 1:1 EtOAc-hexanes and an aqueous 0.5 M EDTA solution (pH 9) was added and the entire mixture was allowed to stir for 1.5 h. The aqueous layer was extracted with three portions of EtOAc, dried (MgSO$_4$), filtered, and the filtrate was concentrated under reduced pressure to provide a green oil. The crude material was subjected to column chromatography on SiO$_2$ (35% EtOAc-hexanes; elution was observed at 285 nm and 228 nm). The product allylic alcohol 6 was a pale yellow oil isolated in 53% yield as a mixture of diastereomers which was taken on to the next step without additional characterization or analysis.

Example 5

Reaction Of Aldehyde Compound 4 With Nucleophilic Alkenyl Species Derived from Alkenyl Iodide 7 with to Provide Allylic Alcohol 8

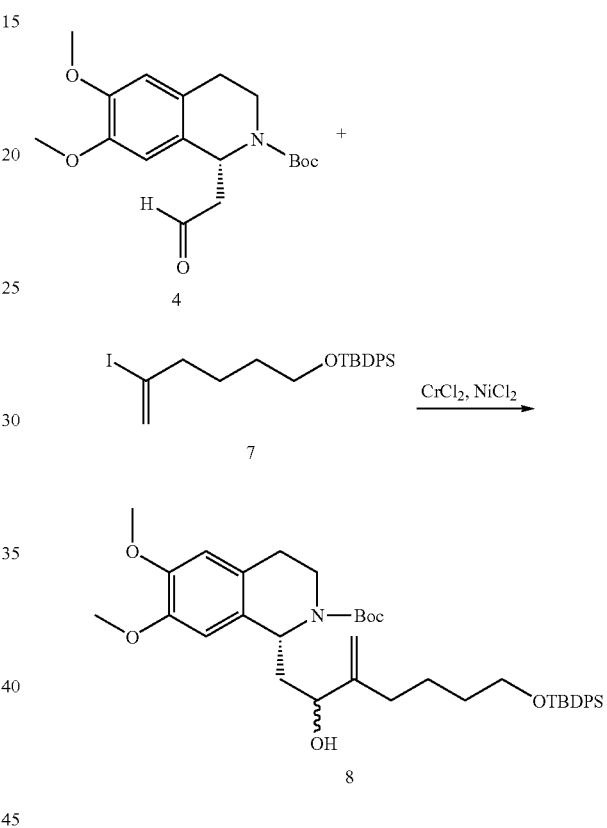

To a neat mixture of the alkenyl iodide 7 (1.0 eq) and the aldehyde compound 4 (1.25 eq.) at room temperature was added 2.5 eq. of chromium chloride doped with 0.5% NiCl$_2$ (w/w). The mixture was vortexed for about 2 min. to provide a homogeneous, green/grey paste and then stirred under nitrogen for an additional 10 min. after which time anhydrous DMF was added to bring the final reaction concentration to 0.32 M. The reaction mixture was deep green in color and was permitted to continue stirring at room temperature for 14 h. Following the allotted time, the reaction mixture was diluted with 1:1 EtOAc-hexanes and an aqueous 0.5 M EDTA solution (pH 9) was added and the entire mixture was allowed to stir for 1.5 h. The aqueous layer was extracted with three portions of EtOAc, dried (MgSO$_4$), filtered, and the filtrate was concentrated under reduced pressure to provide a green oil. The crude material was subjected to column chromatography on SiO$_2$ (20% EtOAc-hexanes to 35% EtOAc-hexanes; elution was observed at 285 nm and 228 nm). The product allylic alcohol 8 was a pale yellow oil isolated in 54% yield as a mixture of diastereomers which was taken on to the next step without additional characterization or analysis.

Example 6

Reaction Of Aldehyde Compound 4 With Nucleophilic Alkenyl Species Derived from Alkenyl Iodide 9 with to Provide Allylic Alcohol 10

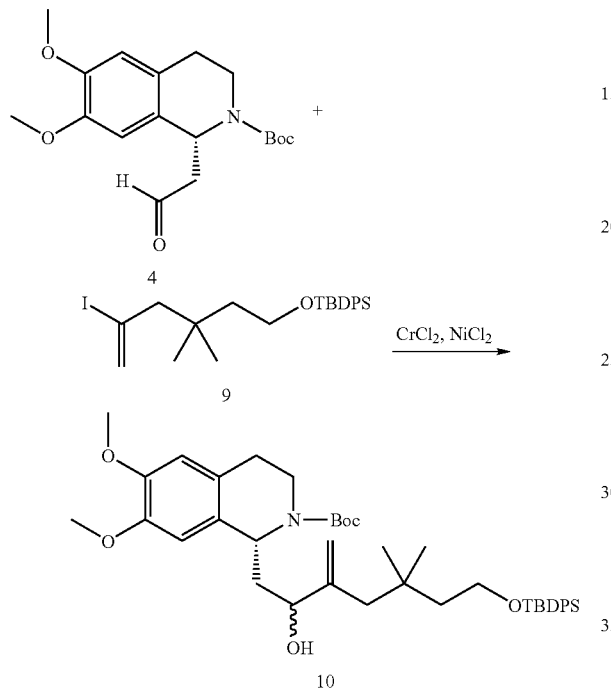

To a neat mixture of the alkenyl iodide 9 (1.5 eq) and the aldehyde 4 (1.0 eq.) at room temperature was added 2.5 eq. of chromium chloride doped with 0.5% NiCl$_2$ (w/w). The mixture was vortexed for about 2 min. to provide a homogeneous, green/grey paste and then stirred under nitrogen for an additional 10 min. after which time anhydrous DMF was added to bring the final reaction concentration to 0.36 M. The reaction mixture was deep green in color and was permitted to continue stirring at room temperature for 14 h. Following the allotted time, the reaction mixture was diluted with 1:1 EtOAc-hexanes and an aqueous 0.5 M EDTA solution (pH 9) was added and the entire mixture was allowed to stir for 1.5 h.

The aqueous layer was extracted with three portions of EtOAc, dried (MgSO$_4$), filtered, and the filtrate was concentrated under reduced pressure to provide a green oil. The crude material was subjected to column chromatography on SiO$_2$ (40% EtOAc-hexanes; elution was observed at 285 nm and 228 nm) to afford the product allylic alcohol 10 as a pale yellow oil that existed as a 1:1 mixture of diastereomers (47%): $^1$H NMR (CD$_2$Cl$_2$) δ 0.94-1.00 (m, 6H), 1.13-1.16 (m, 9H), 1.54-1.57 (m, 9H), 1.67-1.74 (m, 2H), 1.79-1.86 (m, 0.5H), 1.87-1.94 (m, 1H), 1.96-2.05 (m, 0.5H), 2.09-2.24 (m, 2H), 2.66-2.77 (m, 1H), 2.85-2.99 (m, 1H), 3.16-3.22 (m, 0.5H), 3.36-3.44 (m, 0.5H), 3.80-3.92 (m, 8H), 4.01-4.08 (m, 0.5H), 4.12-4.17 (m, 0.5H), 4.30-4.38 (m, 0.5H), 4.66-4.77 (m, 0.5H), 4.86-4.96 (m, 1H), 5.23-5.30 (m, 0.5H), 5.34-5.39 (m, 1H), 5.39-5.43 (m, 0.5H), 6.68-6.72 (m, 1H), 6.73-6.77 (m, 0.5H), 6.77-6.81 (m, 0.5H), 7.43-7.52 (m, 6H), 7.75-7.82 (m, 4H); $^{13}$C NMR (CD$_2$Cl$_2$) δ 19.12, 26.83, 27.33, 27.45, 27.54, 27.59, 28.29, 28.41, 33.46, 33.48, 38.30, 39.45, 43.64, 43.82, 44.93, 45.05, 45.48, 45.95, 50.95, 52.25, 55.89, 55.99, 56.01, 61.14, 69.99, 73.06, 80.03, 80.49, 110.21, 110.56, 111.87, 112.00, 112.02, 112.39, 125.92, 126.32, 126.35, 127.77, 129.57, 129.69, 130.17, 134.15, 135.68, 147.85, 147.88, 147.99, 148.11, 148.71, 149.59, 149.61, 155.79, 156.39.

Example 7

Oxidation Of Allylic Alcohol 6 to Provide First Intermediate 12

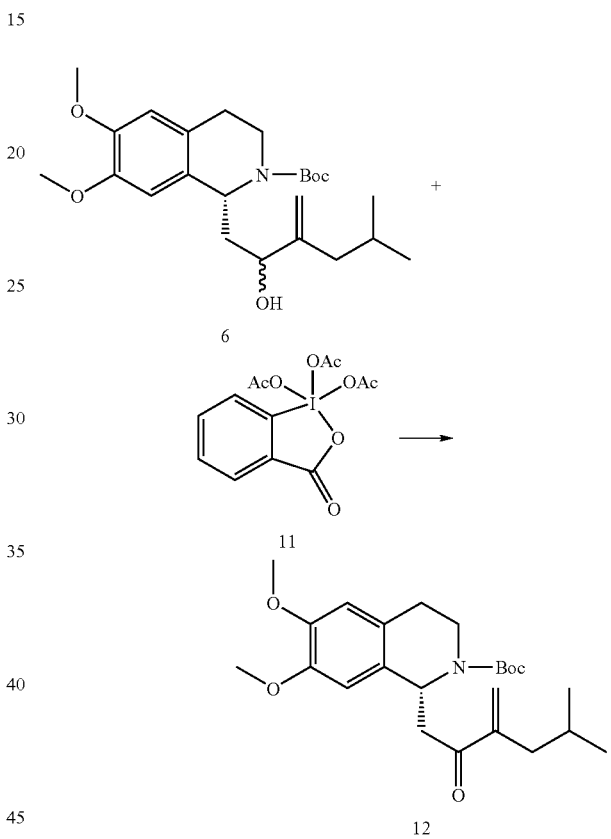

To a 0.1 M solution of allylic alcohol 6 (1.0 eq) in dichloromethane at 0° C. was added 1.1 eq. of the Dess-Martin reagent 11. The reaction mixture was allowed to stir, slowly warming to room temperature over 2.5 h. The reaction was quenched by the addition of saturated aqueous sodium bicarbonate solution and diluted with ethyl acetate. The organic and aqueous layers were partitioned and separated and the aqueous layer extracted with three additional portions of ethyl acetate. The combined organic extracts were washed with brine, dried (MgSO$_4$), filtered, and concentrated under reduced pressure. The crude material was purified by column chromatography on SiO$_2$ (10-30% EtOAc-hexanes, elution was observed at 285 nm and 228 nm). The product first intermediate 12 was a colorless, foul-smelling oil that existed at 26° C. as a 60:40 mixture of rotamers in solution (66%): $^1$H NMR (CDCl$_3$) δ 0.82 (apparent t, J=7.6 Hz, 6H), 1.42 (s, 9H), 1.70 (apparent sept, J=6.62 Hz, 1H), 2.08-2.15 (m, 1H), 2.15-2.24 (m, 1H), 2.62-2.70 (m, 1H), 2.75-2.91 (m, 1H), 2.93-3.07 (m, 1H), 3.07-3.29 (m, 1.6H), 3.30-3.43 (m, 0.4H), 3.79 (s, 3H), 3.81 (s, 3.4H), 4.04-4.16 (m, 0.6H), 5.52-5.62 (m, 1H), 5.69 (s, 1H), 5.90 (s, 0.6H), 6.04 (s, 0.4H), 6.57 (s, 1H), 6.63 (s, 1H); $^{13}$C NMR (CDCl$_3$) δ 22.45, 27.04, 27.25, 28.11, 28.41, 38.01, 39.33, 40.39, 45.20, 45.90, 51.62, 55.92, 55.98, 79.75, 80.23, 109.85, 110.25, 110.28, 111.41, 125.65, 125.72, 126.26, 129.25, 147.57, 147.87, 148.16, 148.29, 148.35, 154.40, 154.51, 199.53; HRMS-(ESI+) calcd for (C$_{24}$H$_{35}$NO$_5$)+H) ([M+H]$^+$ 418.2594. found 418.2590.

Example 8

Oxidation of Allylic Alcohol 8 to Provide First Intermediate 13

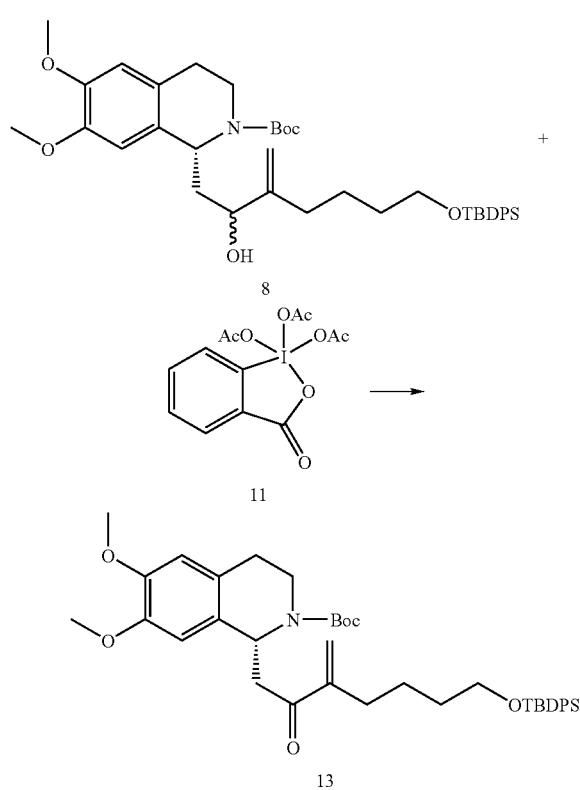

To a 0.1 M solution of 8 (1.0 eq) in dichloromethane at 0° C. was added 1.1 eq. of the Dess-Martin reagent 11. The reaction mixture was allowed to stir, slowly warming to room temperature over 2.5 h. The reaction was quenched by the addition of saturated aqueous sodium bicarbonate solution and diluted with dichloromethane. The organic and aqueous layers were partitioned and separated and the aqueous layer extracted with three additional portions of dichloromethane. The combined organic extracts were washed with brine, dried (MgSO$_4$), filtered, and concentrated under reduced pressure. The crude material was purified by column chromatography on SiO$_2$ (10-50% EtOAc-hexanes, elution was observed at 285 nm and 228 nm). The product first intermediate 13 was a colorless, oil that existed at 26° C. as a 50:50 mixture of rotamers in solution (82%): $^1$H NMR (CD$_2$Cl$_2$) δ 1.19 (s, 9H), 1.55 (s, 9H), 1.63-1.83 (m, 5H), 2.34-2.57 (m, 2H), 2.70-2.85 (m, 1H), 2.85-3.05 (m, 1H), 3.05-3.41 (m, 2.5H), 3.41-3.56 (m, 0.5H), 3.81-3.83 (m, 1H), 3.84 (s, 3H), 3.86 (s, 3H), 3.97-4.08 (m, 0.5H), 4.20-4.35 (m, 0.5H), 5.68 (apparent t, J=6.6 Hz, 1H), 5.87 (s, 1H), 6.09 (s, 0.5H), 6.19 (s, 0.5H), 6.71 (s, 1H), 6.76 (s, 1H), 7.45-7.60 (m, 6H), 7.77-7.95 (m, 4H); $^{13}$C NMR (CD$_2$Cl$_2$) δ 19.19, 24.66, 24.75, 26.83, 28.06, 28.28, 30.57, 32.43, 37.75, 39.20, 45.16, 45.66, 63.84, 79.46, 79.77, 110.21, 110.49, 111.81, 124.37, 124.67, 126.45, 127.76, 129.19, 129.68, 134.13, 135.61, 147.79, 148.19, 149.20, 154.09, 154.41, 199.15, 199.27; HRMS-(ESI+) calcd for (C$_{40}$H$_{53}$NO$_6$Si+H) ([M+H]+672.3720. found 672.3715.

Example 9

Oxidation of Allylic Alcohol 10 to Provide First Intermediate 14

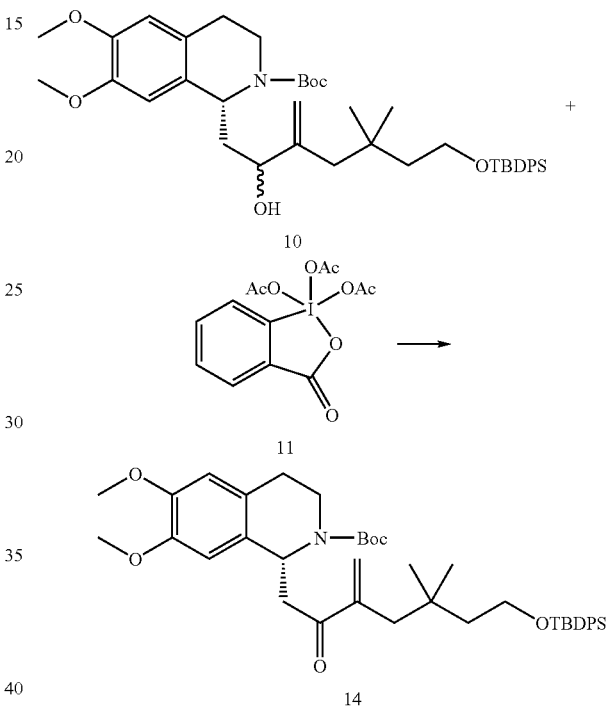

To a 0.1 M solution of allylic alcohol 10 (1.0 eq) in dichloromethane at 0° C. was added 1.1 eq. of the Dess-Martin reagent 11. The reaction mixture was allowed to stir, slowly warming to room temperature over 5 h. The reaction was quenched by the addition of saturated aqueous sodium bicarbonate solution and diluted with dichloromethane. The organic and aqueous layers were partitioned and separated and the aqueous layer extracted with three additional portions of dichloromethane. The combined organic extracts were washed with brine, dried (MgSO$_4$), filtered, and concentrated under reduced pressure. The crude material was purified by column chromatography on SiO$_2$ (10-50% EtOAc-hexanes, elution was observed at 285 nm and 228 nm). The product first intermediate 14 was a yellow foam that existed at 26° C. as a 50:50 mixture of rotamers in solution (93%): $^1$H NMR (CD$_2$Cl$_2$) δ 0.85 (s, 6H), 1.14 (s, 9H), 1.48-1.57 (m, 9H), 1.65 (t, J=7.3 Hz, 2H), 2.30-2.50 (m, 2H), 2.70-2.80 (m, 1H), 2.85-2.98 (m, 1H), 3.07-3.17 (m, 1H), 3.22-3.37 (m, 1.5H), 3.38-3.50 (m, 0.5H), 3.81 (s, 3H), 3.85 (s, 3H), 3.85-3.92 (m, 2H), 3.94-4.02 (m, 0.5H), 4.18-4.25 (m, 0.5H), 5.65-5.72 (m, 1H), 5.74 (s, 1H), 6.07 (s, 0.5H), 6.14 (s, 0.5H), 6.69 (s, 1H), 6.76 (s, 1H), 7.45-7.54 (m, 6H), 7.77-7.82 (m, 4H); $^{13}$C NMR (CD$_2$Cl$_2$) δ 19.09, 26.80, 26.92, 26.97, 28.13, 28.22, 28.28, 33.22, 37.94, 39.39, 41.79, 41.87, 44.49, 45.33, 46.02, 51.16, 51.44, 55.79, 55.83, 61.05, 79.47, 79.76, 110.18, 110.51, 111.74, 126.40, 127.26, 127.36, 127.76, 129.48, 129.69, 134.09, 135.66, 146.93, 147.06, 147.78, 148.10, 154.16, 154.47, 199.36; HRMS-(ESI+) calcd for ($C_{42}H_{57}NO_6Si$—$C_5H_9O_2$(Boc)+H) ([M-Boc+H]$^+$ 600.3509. found 600.3496.

Example 10

Removal the Boc Protecting Group From First Intermediate 12 and Amino Cyclization Provide (+)-Tetrabenazine XVII

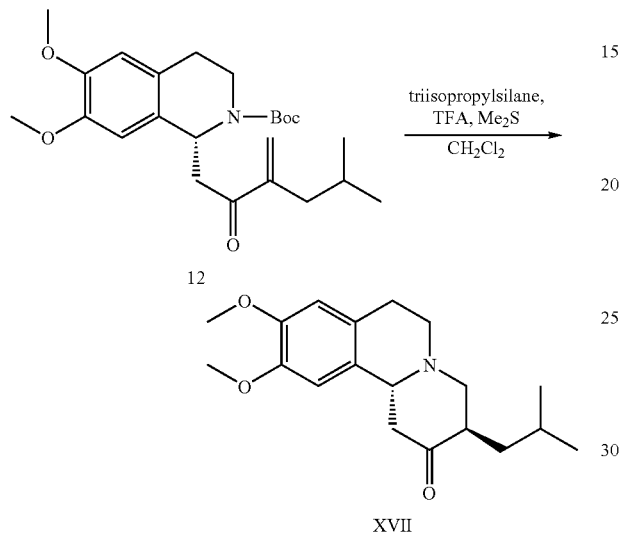

tion and concentrated under reduced pressure to remove the majority of the dimethylsulfide. The mixture was extracted with five portions of dichloromethane, and the combined organic extracts were washed with brine, dried (MgSO$_4$), filtered and concentrated under reduced pressure to provide the crude product as a yellow solid. The crude product was recrystallized from 3.5% dimethoxyethane in hexanes. The resulting colorless crystals were washed with hexanes to provide pure (+)-tetrabenazine (XVII) 46%: mp 126.0° C. (3.5% DME-hexanes) (a crystal polymorph was observed at 116° C.); $[\alpha]^{26}_D$ +37.2 (c 0.41, $CH_2Cl_2$); $^1$H NMR ($CD_2Cl_2$) δ 0.89 (apparent t, J=7.2 Hz, 6H), 0.98 (ddd, J=12, 6.0, 4.0 Hz, 1H), 1.59-1.68 (m, 1H), 1.74 (ddd, J=12, 5.9, 5.7 Hz, 1H), 2.32 (apparent t, J=11.7 Hz, 1H), 2.46 (apparent t, J=12.3 Hz, 1H), 2.55 (ddd, J=12, 10.0, 3.8 Hz, 1H), 2.65-2.73 (m, 2H), 2.83 (dd, J=5.5, 2.8 Hz, 1H), 2.97-3.07 (m, 1H), 3.07-3.14 (m, 1H), 3.25 (dd, J=9.7, 6.3 Hz, 1H), 3.47 (apparent d, J=12 Hz, 1H), 3.75 (s, 3H), 3.77 (s, 3H), 6.55 (s, 1H), 6.60 (s, 1H) $^{13}$C NMR ($CD_2Cl_2$) δ 21.98, 23.02, 25.51, 29.46, 35.16, 47.47, 47.63, 50.47, 55.87, 56.01, 61.47, 62.46, 108.46, 111.72, 126.37, 128.96, 147.65, 147.98, 209.72; HRMS-(ESI+) calcd for ($C_{19}H_{27}NO_3$+H) ([M+H]$^+$ 318.2069. found 318.2082.

Example 11

Removal the Boc Protecting Group from First Intermediate 13 and Amino Cyclization Provide (+)-TBZ Compound 15

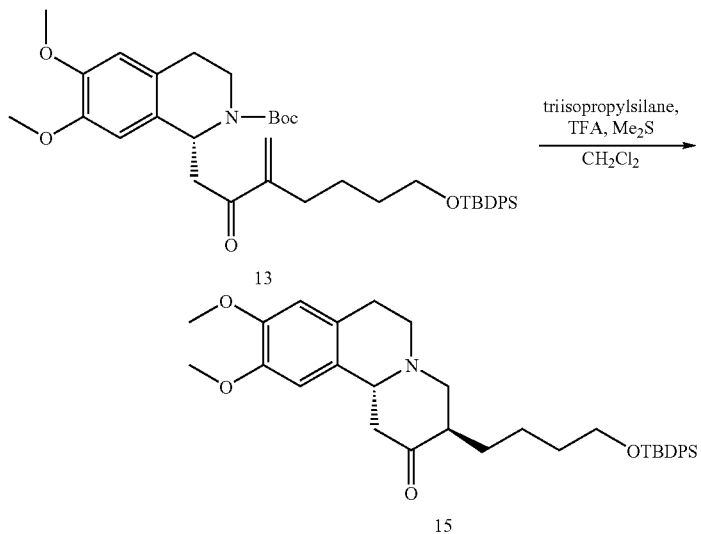

First intermediate 12 (1.0 eq) was dissolved in 10% Me$_2$S-dichloromethane to provide an 82 mM solution. The solution was cooled to 0° C. and triisopropylsilane (1.1 eq.) followed by TFA (precooled to 0° C.) was added to the reaction mixture to provide a final concentration of 41 mM. The reaction mixture was permitted to stir at 0° C. for 1 h. Following the allotted time the reaction mixture was quenched at 0° C. by the addition of saturated aqueous potassium carbonate solu- The first intermediate starting material 13 (1.0 eq) was dissolved in 10% Me$_2$S-dichloromethane to provide an 26 mM solution. The solution was cooled to 0° C. and triisopropylsilane (1.1 eq.) followed by TFA (precooled to 0° C.) was added to the reaction mixture to provide a final concentration of 13 mM. The reaction mixture was permitted to stir at 0° C. for 1 h. Following the allotted time the reaction mixture was quenched at 0° C. by the addition of saturated aqueous potassium carbonate solution and concentrated under reduced pressure to remove the majority of the dimethylsulfide. The mixture was extracted with five portions of dichloromethane, and the combined organic extracts were washed with brine, dried (MgSO$_4$), filtered and concentrated under reduced pressure to provide an orange oil. The isolated material was immediately subjected to purification by flash chromatography on SiO$_2$ (20-30% EtOAc-hexanes, elution was observed at 285 nm and 228 nm). The semipure product (existed as a mixture of diastereomers heavily favoring the desired product) was subjected to crystallization from 3.5% dimethoxyethane in hexanes over several days. The resulting colorless crystals were washed with hexanes to provide (+)-TBZ compound 15 as a single diastereomer 42%: $[\alpha]^{26}{}_D$ +40.1 (c 0.63, CH$_2$Cl$_2$); $^1$H NMR (CD$_2$Cl$_2$) δ 1.14 (s, 9H), 1.18-1.30 (m, 1H), 1.45-1.56 (m, 2H), 1.60-1.75 (m, 2H), 1.86-1.98 (m, 1H), 2.41 (apparent t, J=11.4 Hz, 1H), 2.47 (apparent t, J=12.6 Hz, 1H), 2.59-2.82 (m, 3H), 2.93 (dd, J=13.1, 2.8 Hz, 1H), 3.06-3.20 (m, 2H), 3.34 (dd, J=9.6, 6.1 Hz, 1H), 3.55 (apparent d, J=11.6 Hz, 1H), 3.78 (apparent t, J=6.3 Hz, 2H), 3.84 (s, 3H), 3.85 (s, 3H), 6.64 (s, 1H), 6.69 (s, 1H), 7.40-7.53 (m, 6H), 7.70-7.81 (m, 4H); $^{13}$C NMR (CD$_2$Cl$_2$) δ 19.14, 23.43, 25.98, 26.74, 29.47, 32.77, 47.55, 49.42, 50.44, 55.74, 55.86, 61.06, 62.36, 63.81, 108.31, 111.68, 126.31, 127.68, 128.91, 129.60, 134.15, 135.59, 147.59, 147.90, 209.36; HRMS-(ESI+) calcd for (C$_{35}$H$_{15}$NO$_4$Si+H) ([M+H]$^+$ 572.3196. found 572.3187.

Example 12

Removal the Boc Protecting Group from First Intermediate 14 and Amino Cyclization Provide (+)-TBZ Compound 16

The starting material 14 (1.0 eq) was dissolved in 10% Me$_2$S-dichloromethane to provide a 176 mM solution of the starting material. The solution was cooled to 0° C. and triisopropylsilane (1.1 eq.) followed by TFA (precooled to 0° C.) was added to the reaction mixture to provide a final concentration of 88 mM. The reaction mixture was permitted to stir at 0° C. for 1 h. Following the allotted time the reaction mixture was quenched at 0° C. by the addition of saturated aqueous potassium carbonate solution and concentrated under reduced pressure to remove the majority of the dimethylsulfide. The mixture was extracted with five portions of dichloromethane, and the combined organic extracts were washed with brine, dried (MgSO$_4$), filtered and concentrated under reduced pressure to provide a yellow foam. The crude product was purified by flash chromatography on SiO$_2$ (0.2% triethylamine-10% EtOAc-89.8% hexanes to 0.2% triethylamine-50% EtOAc-49.8% hexanes, elution was observed at 285 nm and 228 nm). The product (+)-TBZ compound 16 was a colorless foam consisting of only the desired diastereomer 73%: $^1$H NMR (CD$_2$Cl$_2$) δ 0.79 (dd, J=13.8, 3.8 Hz, 1H), 0.92 (s, 6H), 1.14 (s, 9H), 1.59-1.72 (m, 2H), 2.27 (dd, J=13.2, 5.1 Hz, 1H), 2.52-2.65 (m, 2H), 2.68-2.82 (m, 2H), 2.94 (dd, J=13.0, 3.0 Hz, 1H), 3.06-3.18 (m, 2H), 3.25 (dd, J=9.8, 6.3 Hz), 3.55 (dd, J=11.6, 1.8 Hz, 1H), 3.83-3.88 (m, 8H), 6.65 (s, 1H), 6.69 (s, 1H), 7.44-7.53 (m, 6H), 7.74-7.82 (m, 4H); $^{13}$C NMR (CD$_2$Cl$_2$) δ 19.09, 26.79, 27.10, 29.48, 32.31, 36.90, 44.38, 46.02, 47.45, 50.15, 55.77, 55.91, 61.09, 62.53, 63.50, 108.38, 111.75, 126.30, 127.74, 128.93, 129.67, 134.13, 135.65, 147.66, 147.98, 208.73; HRMS-(ESI+) calcd for (C$_{37}$H$_{19}$NO$_4$Si+H) ([M+H]$^+$ 600.3509. found 600.3499.

Example 13

Ketalization of TBZ Compound 15 to Provide Ketal 17

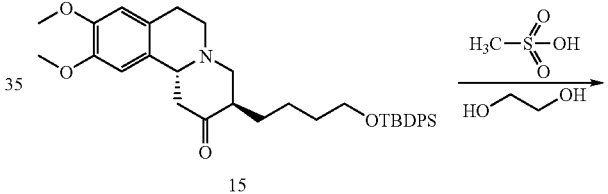

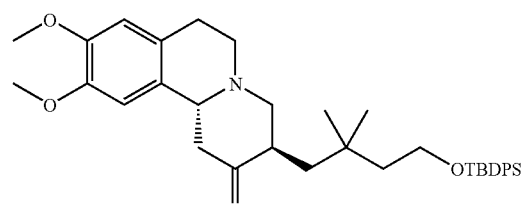

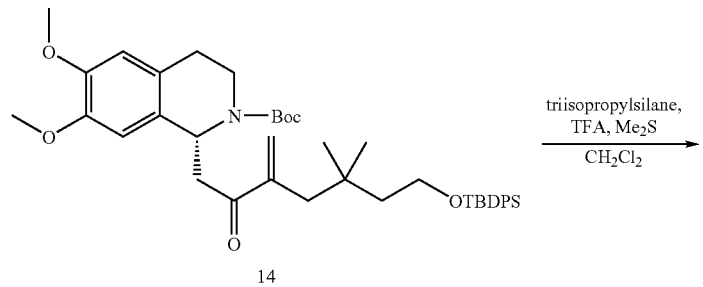

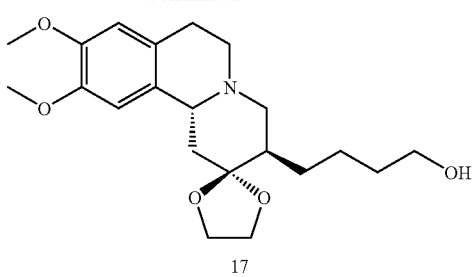

17

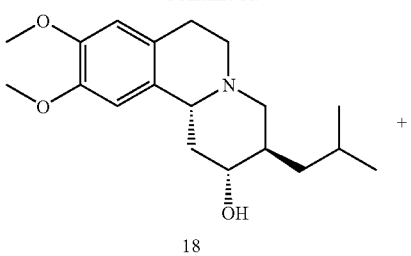

18

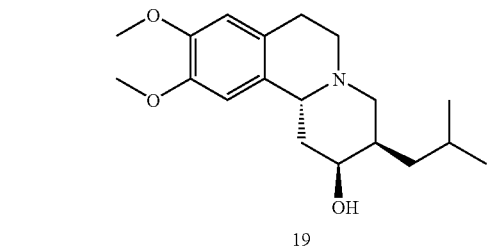

19

To an 87 mM solution of the TBZ compound 15 (1.0 eq) in ethylene glycol was added methane sulfonic acid (1.76 eq). The reaction mixture was heated to and maintained at 85° C. for 20 h in a sealed vessel. Following the allotted time, the reaction mixture was quenched be the addition of 1 mL of saturated aqueous potassium carbonate solution and EtOAc was added. The reaction mixture was stirred for an additional hour at room temperature after which time the aqueous and organic layers were partitioned and separated. The aqueous layer was extracted with three portions of $CH_2Cl_2$ and the combined organic extracts were dried ($MgSO_4$), filtered, and concentrated under reduced pressure to provide a yellow oil. Purification of the crude material was undertaken by flash chromatography on $SiO_2$ (1% triethylamine-DCM to 1% triethylamine-9% methanol-90% DCM; elution was observed at 284 nm and 240 nm). Pools believed to contain the desired product were collected to provide ketal 17 as a colorless oil 73%: $^1$H NMR ($CD_2Cl_2$) δ 1.03-1.15 (m, 1H), 1.20-1.35 (m, 2H), 1.37-1.61 (m, 4H), 1.87-1.99 (m, 1H), 2.08-2.17 (br s, 1H), 2.20-2.29 (m, 2H), 2.42-2.51 (m, 1H), 2.55-2.64 (m, 1H), 2.92-3.03 (m, 3H), 3.27 (apparent d, J=11 Hz, 1H), 3.57 (apparent t, J=6.3 Hz, 2H), 3.758 (s, 3H), 3.764 (s, 3H), 3.92-4.00 (m, 2H), 4.00-4.09 (m, 2H), 6.56 (s, 1H), 6.57 (s, 1H); $^{13}$C NMR ($CD_2Cl_2$) δ 23.74, 25.30, 29.31, 33.25, 41.00, 43.90, 55.74, 56.07, 58.68, 59.82, 62.64, 63.68, 65.17, 63.35, 108.50, 109.65, 111.78, 126.82, 129.81, 147.31, 147.67; LRMS-(ESI+) calcd for ($C_{21}H_{31}NO_5$+H) ([M+H]$^+$ 378.23. found 378.25.

Example 14

Reduction of (+)-tetrabenazine XVII To a Diasteromeric Mixture of Dihydrotetrabenazine Compounds 18 and 19

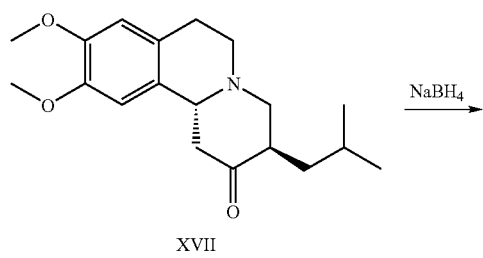

XVII

→ NaBH$_4$

To a 0.11 M solution of (+)-TBZ (XVII) in ethanol at 0° C. was added NaBH$_4$ (2.85 eq). The reaction mixture was allowed to stir for 60 min. at room temperature. The solvent was carefully removed under reduced pressure, and the residue was taken up in dichloromethane and washed with three portions of saturated aqueous $K_2CO_3$. The aqueous washings were back extracted with two portions of dichloromethane. The combined organic extracts were dried ($MgSO_4$), filtered, and concentrated under reduced pressure to provide a colorless oil that crystallized on standing under high vacuum. Purification of the crude product was achieved by chromatography on $SiO_2$ (2.5-5% MeOH—$CH_2Cl_2$, elution was observed at 285 nm) UV active fractions were reanalyzed by TLC. Two products, 18 and 19, were isolated from this procedure. The major product 18 was a colorless solid 74%: $[\alpha]^{26}_D$ +48 (c 0.30, $CH_2Cl_2$) $^1$H NMR ($CD_2Cl_2$) δ 0.93 (d, J=6.6 Hz, 3H), 0.95 (d, J=6.6 Hz, 3H), 1.04 (ddd, J=14.6, 8.7, 4.3 Hz, 1H), 1.42 (dd, J=20.2, 11.4 Hz, 1H), 1.59 (ddd, J=13.7, 9.6, 3.3 Hz, 1H), 1.64-1.78 (m, 2H), 1.96 (apparent t, J=11.4 Hz, 1H), 2.27 (br s, 1H), 2.40-2.48 (m, 1H), 2.54 (ddd, J=12.3, 3.7, 2.3 Hz, 1H), 2.60-2.67 (m, 1H), 2.95-3.09 (m, 3H), 3.11 (apparent d, J=11.1 Hz, 1H), 3.35 (ddd, J=10.4, 10.4, 4.5 Hz, 1H), 3.80-3.81 (m, 6H), 6.60 (s, 1H), 6.69 (s, 1H); $^{13}$C NMR ($CD_2Cl_2$) δ 21.61, 24.02, 25.33, 29.30, 39.68, 40.81, 41.58, 51.83, 55.74, 55.91, 60.02, 60.92, 74.32, 108.42, 111.73, 126.68, 129.76, 147.35, 147.61; HRMS-(ESI+) calcd for ($C_{19}H_{29}NO_3$+H) ([M+H]$^+$ 320.2226. found 320.2242. The minor product 19 was a yellow oil 4%: $^1$H NMR ($CD_2Cl_2$) δ 0.94 (d, J=6.6 Hz, 3H), 0.96 (d, J=6.6 Hz, 3H), 1.13-1.20 (m, 1H), 1.24-1.34 (m, 2H), 1.60-1.77 (m, 2H), 1.89-2.00 (m, 1H) 2.36-2.44 (m, 2H), 2.53 (ddd, J=10.5, 10.5, 3.8 Hz, 1H), 2.58-2.70 (m, 2H), 2.91-2.98 (m, 1H), 2.98-3.09 (m, 1H), 3.48 (apparent d, J=11.6 Hz, 1H), 3.80-3.82 (apparent s, 6H), 4.07 (apparent d, J=3.1 Hz, 1H), 6.60 (s, 1H), 6.68 (s, 1H); $^{13}$C NMR ($CD_2Cl_2$) δ 22.74, 22.81, 24.87, 29.30, 37.83, 38.87, 39.42, 52.44, 55.76, 55.96, 56.32, 56.43, 67.88, 108.45, 111.78, 127.18, 130.38, 147.30, 147.54.

Example 15

Reduction of TBZ Compound 15 DTBZ Compound 20

To a 0.1 M solution of TBZ compound 15 in ethanol at 0° C. was added NaBH, (2.85 eq). The reaction mixture was allowed to stir for 60 min. at room temperature. The excess solvent was carefully removed under reduced pressure, and the residue was taken up in dichloromethane and washed with three portions of saturated aqueous $K_2CO_3$. The aqueous washings were back extracted with two portions of dichloromethane. The combined organic extracts were dried ($MgSO_4$), filtered, and concentrated under reduced pressure to provide a yellow foam. Purification of the crude product was achieved by chromatography on $SiO_2$ (2.5-5% MeOH—$CH_2Cl_2$, elution was observed at 285 nm). The product DTBZ compound 20 was a colorless foam 78%: $^1H$ NMR ($CD_2Cl_2$) δ 1.09-1.22 (m, 11H), 1.44 (dd, J=20.1, 11.6 Hz, 2H), 1.55-1.72 (m, 4H), 1.78-1.88 (m, 1H), 2.02 (apparent t, J=11.4 Hz, 1H), 2.46 (ddd, J=4.6, 11.3, 10.3 Hz, 1H), 2.57 (ddd, J=13.1, 3.8, 2.5 Hz, 1H), 2.65 (dd, J=14.3, 4.0 Hz, 1H), 2.94-3.10 (m, 3H), 3.14 (apparent d, J=11.1 Hz, 1H), 3.40 (ddd, J=9.5, 9.5, 4.6 Hz, 1H), 3.76 (apparent t, J=6.3 Hz, 2H), 3.83 (apparent s, 6H), 6.63 (s, 1H), 6.73 (s, 1H), 7.42-7.49 (m, 6H), 7.71-7.76 (m, 4H); $^{13}C$ NMR ($CD_2Cl_2$) δ 19.17, 23.21, 26.75, 29.38, 29.79, 33.03, 40.89, 43.88, 51.86, 55.76, 55.94, 59.78, 60.95, 63.93, 73.92, 108.48, 111.76, 126.75, 127.69, 129.61, 129.81, 134.23, 135.62, 147.38, 147.63; HRMS-(ESI+) calcd for ($C_{35}H_{17}NO_4Si+H$) ([M+H]$^+$ 574.3353. found 574.3333.

The foregoing examples are merely illustrative, serving to illustrate only some of the features of the invention. The appended claims are intended to claim the invention as broadly as it has been conceived and the examples herein presented are illustrative of selected embodiments from a manifold of all possible embodiments. Accordingly, it is the Applicants' intention that the appended claims are not to be limited by the choice of examples utilized to illustrate features of the present invention. As used in the claims, the word "comprises" and its grammatical variants logically also subtend and include phrases of varying and differing extent such as for example, but not limited thereto, "consisting essentially of" and "consisting of." Where necessary, ranges have been supplied, those ranges are inclusive of all sub-ranges there between. It is to be expected that variations in these ranges will suggest themselves to a practitioner having ordinary skill in the art and where not already dedicated to the public, those variations should where possible be construed to be covered by the appended claims. It is also anticipated that advances in science and technology will make equivalents and substitutions possible that are not now contemplated by reason of the imprecision of language and these variations should also be construed where possible to be covered by the appended claims.

The invention claimed is:

1. A tetrahydroisoquinoline compound having structure III wherein $R^1$-$R^4$ are independently hydrogen or an isotope thereof, a halogen atom, a $C_1$-$C_{20}$ aliphatic radical, a $C_2$-$C_{20}$ cycloaliphatic radical, or a $C_2$-$C_{20}$ aromatic radical, wherein at least one of $R^1$-$R^4$ is not hydrogen; $R^5$-$R^{11}$ are independently hydrogen or an isotope thereof, a $C_1$-$C_{20}$ aliphatic radical, a $C_2$-$C_{20}$ cycloaliphatic radical, or a $C_2$-$C_{20}$ aromatic radical; and $P^1$ is a protecting group.

2. The tetrahydroisoquinoline compound according to claim 1, wherein said protecting group $P^1$ comprises a carbonyl group.

3. The tetrahydroisoquinoline compound according to claim 1, wherein the protecting group $P^1$ is selected from the group consisting of Boc, Fmoc, Cbz, Alloc, benzyl, and t-butyl.

4. The tetrahydroisoquinoline compound according to claim 1, wherein the protecting group $P^1$ is a Boc group.

5. The tetrahydroisoquinoline compound according to claim 1, which is enantiomerically enriched.

6. The tetrahydroisoquinoline compound according to claim 5, at least 95 mole % of which is comprised of an enantiomer having the R configuration at ring position-12.

7. The tetrahydroisoquinoline compound according to claim 5, at least 95 mole % of which is comprised of an enantiomer having the S configuration at ring position-12.

8. A tetrahydroisoquinoline compound having structure XI wherein $R^1$-$R^4$ are independently hydrogen or an isotope thereof, a halogen atom, a $C_1$-$C_{20}$ aliphatic radical, a $C_2$-$C_{20}$ cycloaliphatic radical, or a $C_2$-$C_{20}$ aromatic radical, wherein at least one of $R^1$-$R^4$ is not hydrogen; and $R^5$-$R^{11}$ are independently hydrogen or an isotope thereof, a $C_1$-$C_{20}$ aliphatic radical, a $C_2$-$C_{20}$ cycloaliphatic radical, or a $C_2$-$C_{20}$ aromatic radical.

9. A tetrahydroisoquinoline compound having structure XII

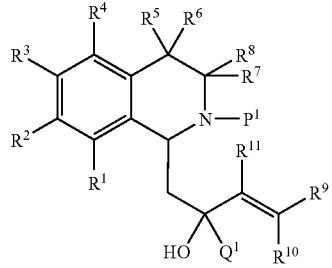

wherein $R^1$-$R^4$ are independently hydrogen or an isotope thereof, a halogen atom, a $C_1$-$C_{20}$ aliphatic radical, a $C_2$-$C_{20}$ cycloaliphatic radical, or a $C_2$-$C_{20}$ aromatic radical, wherein at least one of $R^1$-$R^4$ is not hydrogen; $R^5$-$R^{11}$ are independently hydrogen or an isotope thereof, a $C_1$-$C_{20}$ aliphatic radical, a $C_2$-$C_{20}$ cycloaliphatic radical, or a $C_2$-$C_{20}$ aromatic radical; $P^1$ is a protecting group; and $Q^1$ is hydrogen or an isotope thereof.

10. The tetrahydroisoquinoline compound according to claim 9, which is enantiomerically enriched.

11. The tetrahydroisoquinoline compound according to claim 10, at least 95 mole % of which is comprised of an enantiomer having the R configuration at ring position-12.

12. The tetrahydroisoquinoline compound according to claim 10, at least 95 mole % of which is comprised of an enantiomer having the S configuration at ring position-12.

13. A tetrahydroisoquinoline compound having structure XIII

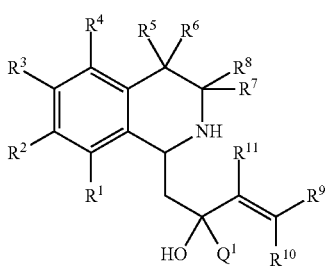

wherein $R^1$-$R^4$ are independently hydrogen or an isotope thereof, a halogen atom, a $C_1$-$C_{20}$ aliphatic radical, a $C_2$-$C_{20}$ cycloaliphatic radical, or a $C_2$-$C_{20}$ aromatic radical, wherein at least one of $R^1$-$R^4$ is not hydrogen; $R^5$-$R^{11}$ are independently hydrogen or an isotope thereof, a $C_1$-$C_{20}$ aliphatic radical, a $C_2$-$C_{20}$ cycloaliphatic radical, or a $C_2$-$C_{20}$ aromatic radical; and $Q^1$ is hydrogen or an isotope thereof.

14. A tetrahydroisoquinoline compound having structure VII

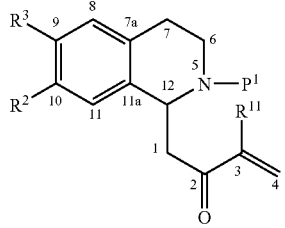

wherein $R^2$-$R^3$ are independently hydrogen or an isotope thereof, a halogen atom, a $C_1$-$C_{20}$ aliphatic radical, a $C_2$-$C_{20}$ cycloaliphatic radical, or a $C_2$-$C_{20}$ aromatic radical, wherein at least one of $R^2$-$R^3$ is not hydrogen; $R^{11}$ is hydrogen or an isotope thereof, a $C_1$-$C_{20}$ aliphatic radical, a $C_2$-$C_{20}$ cycloaliphatic radical, or a $C_2$-$C_{20}$ aromatic radical; and $P^1$ is a protecting group.

15. The tetrahydroisoquinoline compound according to claim 14, which is enantiomerically enriched.

16. The tetrahydroisoquinoline compound according to claim 15, at least 95 mole % of which is comprised of an enantiomer having the R configuration at ring position-12.

17. The tetrahydroisoquinoline compound according to claim 15, at least 95 mole % of which is comprised of an enantiomer having the S configuration at ring position-12.

18. A tetrahydroisoquinoline compound having structure XIV

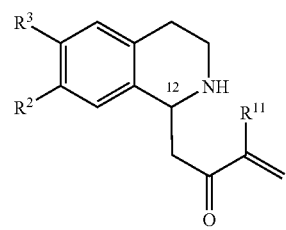

wherein $R^2$-$R^3$ are independently hydrogen or an isotope thereof, a halogen atom, a $C_1$-$C_{20}$ aliphatic radical, a $C_2$-$C_{20}$ cycloaliphatic radical, or a $C_2$-$C_{20}$ aromatic radical, wherein at least one of $R^2$-$R^3$ is not hydrogen; and $R^{11}$ is hydrogen or an isotope thereof, a $C_1$-$C_{20}$ aliphatic radical, a $C_2$-$C_{20}$ cycloaliphatic radical, or a $C_2$-$C_{20}$ aromatic radical.

19. The tetrahydroisoquinoline compound according to claim 18, which is enantiomerically enriched.

20. The tetrahydroisoquinoline compound according to claim 19, at least 95 mole % of which is comprised of an enantiomer having the R configuration at ring position-12.

21. The tetrahydroisoquinoline compound according to claim 19, at least 95 mole % of which is comprised of an enantiomer having the S configuration at ring position-12.

22. A tetrahydroisoquinoline compound having structure XV

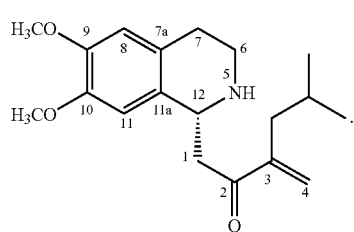
XV
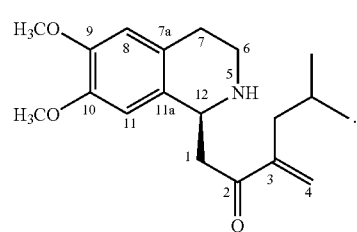
XVI
23. A tetrahydroisoquinoline compound having structure XVI
* * * * *

UNITED STATES PATENT AND TRADEMARK OFFICE
CERTIFICATE OF CORRECTION

PATENT NO. : 8,008,500 B2
APPLICATION NO. : 11/760372
DATED : August 30, 2011
INVENTOR(S) : Rishel et al.

It is certified that error appears in the above-identified patent and that said Letters Patent is hereby corrected as shown below:

In Column 25, Line 2, delete "VIII" and insert -- VI --, therefor.

In Column 31, in Table 10, Under "$R^{11}$", Line 5, delete "pentyl" and insert -- 1-pentyl --, therefor.

In Column 44, in Table 14, Under "Structure", Line 2, delete " 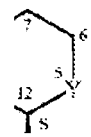 " and insert -- 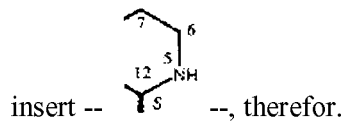 --, therefor.

In Column 45, Line 59, delete "XVI." and insert -- XV. --, therefor.

In Column 48, Line 15, delete "($[M+H]^+$" and insert -- $[M+H]^+$ --, therefor.

In Column 48, Line 15, delete "394.22." and insert -- 394.22, --, therefor.

In Column 53, Line 7, delete "($C_{24}H_{35}NO_5$)+H) ($[M+H]^+$" and insert -- ($C_{24}H_{35}NO_5$+H) $[M+H]^+$ --, therefor.

In Column 53, Line 7, delete "418.2594." and insert -- 418.2594, --, therefor.

In Column 54, Line 6, delete "([M+H]+672.3720." and insert -- $[M+H]^+$ 672.3720, --, therefor.

In Column 55, Line 4, delete "$[M-Boc+H]^+$" and insert -- $[M-Boc+H]^+$ --, therefor.

Signed and Sealed this
Twelfth Day of June, 2012

David J. Kappos
*Director of the United States Patent and Trademark Office*

CERTIFICATE OF CORRECTION (continued)
U.S. Pat. No. 8,008,500 B2

In Column 55, Line 4, delete "600.3509." and insert -- 600.3509, --, therefor.

In Column 56, Line 27, delete "([M+H]$^+$" and insert -- [M+H]$^+$ --, therefor.

In Column 56, Line 27, delete "318.2069." and insert -- 318.2069, --, therefor.

In Column 57, Line 32, delete "([M+H]$^+$" and insert -- [M+H]$^+$ --, therefor.

In Column 57, Line 33, delete "572.3196." and insert -- 572.3196, --, therefor.

In Column 58, Line 27, delete "($C_{37}H_{19}NO_4Si$+H) [M+H]$^+$ 600.3509." and insert -- ($C_{37}H_{49}NO_4Si$+H) ([M+H]$^+$ 600.3509, --, therefor.

In Column 59, Line 44, delete "([M+H]$^+$" and insert -- [M+H]$^+$ --, therefor.

In Column 59, Line 44, delete "378.23." and insert -- 378.23, --, therefor.

In Column 60, Line 55, delete "([M+H]$^+$" and insert -- [M+H]$^+$ --, therefor.

In Column 60, Line 55, delete "320.2226." and insert -- 320.2226, --, therefor.

In Column 61, Line 29, delete "NaBH," and insert -- $NaBH_4$ --, therefor.

In Column 61, Line 52, delete "([M+H]$^+$" and insert -- [M+H]$^+$ --, therefor.

In Column 61, Line 52, delete "574.3353." and insert -- 574.3353, --, therefor.